United States Patent [19]
Rosenschein et al.

[11] Patent Number: 6,113,558
[45] Date of Patent: Sep. 5, 2000

[54] PULSED MODE LYSIS METHOD

[75] Inventors: Uri Rosenschein, Kefar Daniel; Yoram Eshel, Tel Aviv; Vladimir Furman, Ashelon; Efim Kerner, Rehovot, all of Israel

[73] Assignee: Angiosonics Inc., Morrisville, N.C.

[21] Appl. No.: 08/939,289

[22] Filed: Sep. 29, 1997

[51] Int. Cl.$^7$ ............................................. A61N 7/00
[52] U.S. Cl. ................................... 601/2; 606/128
[58] Field of Search ...................... 601/2–4; 606/1, 606/128, 169; 604/22; 600/439

[56] References Cited

U.S. PATENT DOCUMENTS

| | | | |
|---|---|---|---|
| 3,636,943 | 1/1972 | Balamuth | 601/2 |
| 3,941,122 | 3/1976 | Jones | 601/2 |
| 5,069,664 | 12/1991 | Guess et al. | 604/22 |
| 5,720,287 | 2/1998 | Chapelon et al. | 601/2 |

*Primary Examiner*—Ruth S. Smith
*Attorney, Agent, or Firm*—Stroock & Stroock & Lavan LLP

[57] ABSTRACT

An apparatus and method for the application of ultrasound to a location within the body is provided. The apparatus can advantageously operate at a pulse duration below about 100 milliseconds and in the range 0.1 milliseconds to 100 milliseconds and a pulse repetition period below about 1 second and in the range of 1 millisecond to 1 second. Duty ratios over 5 and preferably over 8 are also advantageous. Therapeutic applications of ultrasound such as for assisting in the treatment of medical conditions such as cancer and/or other ailments are also provided.

32 Claims, 32 Drawing Sheets

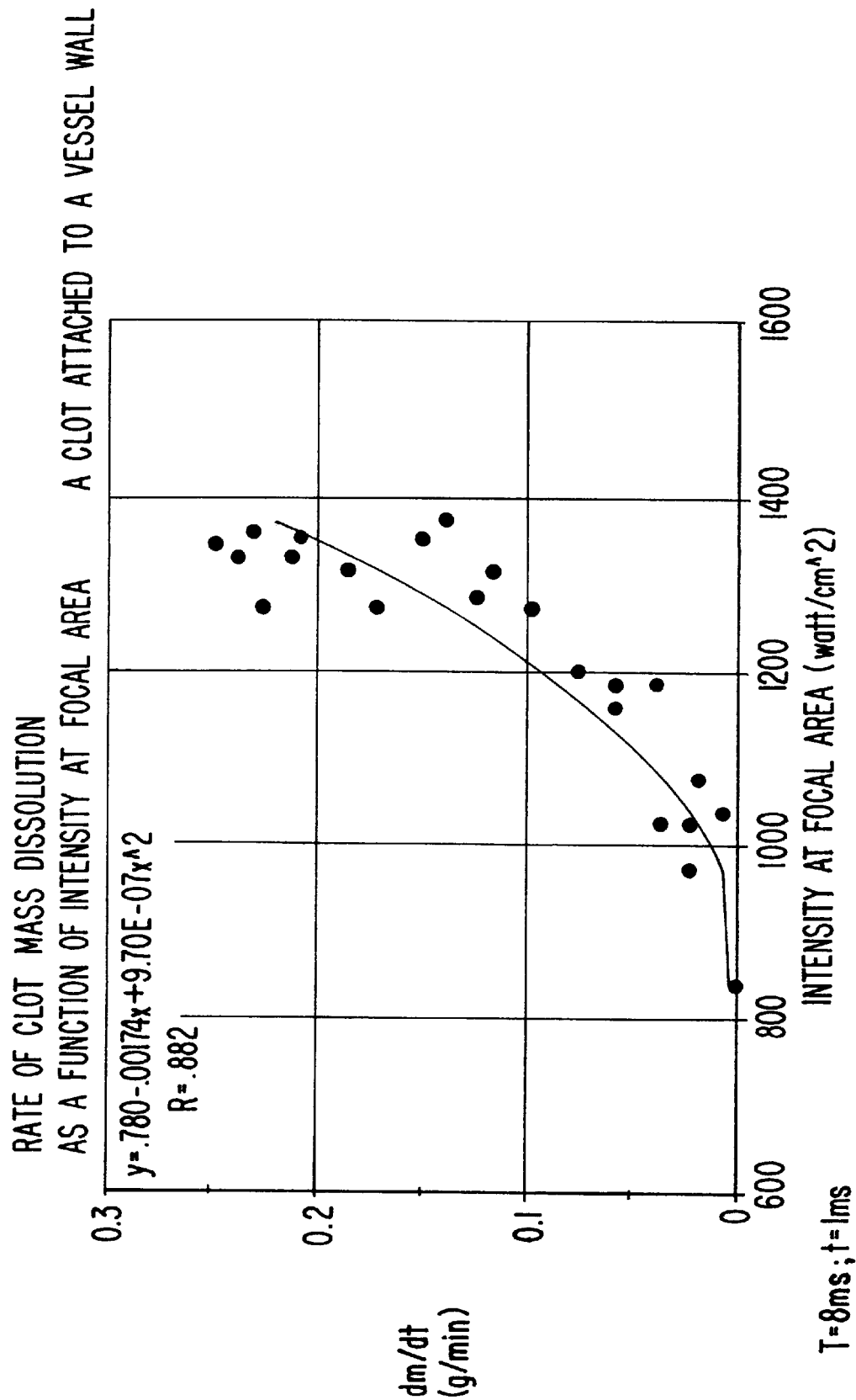

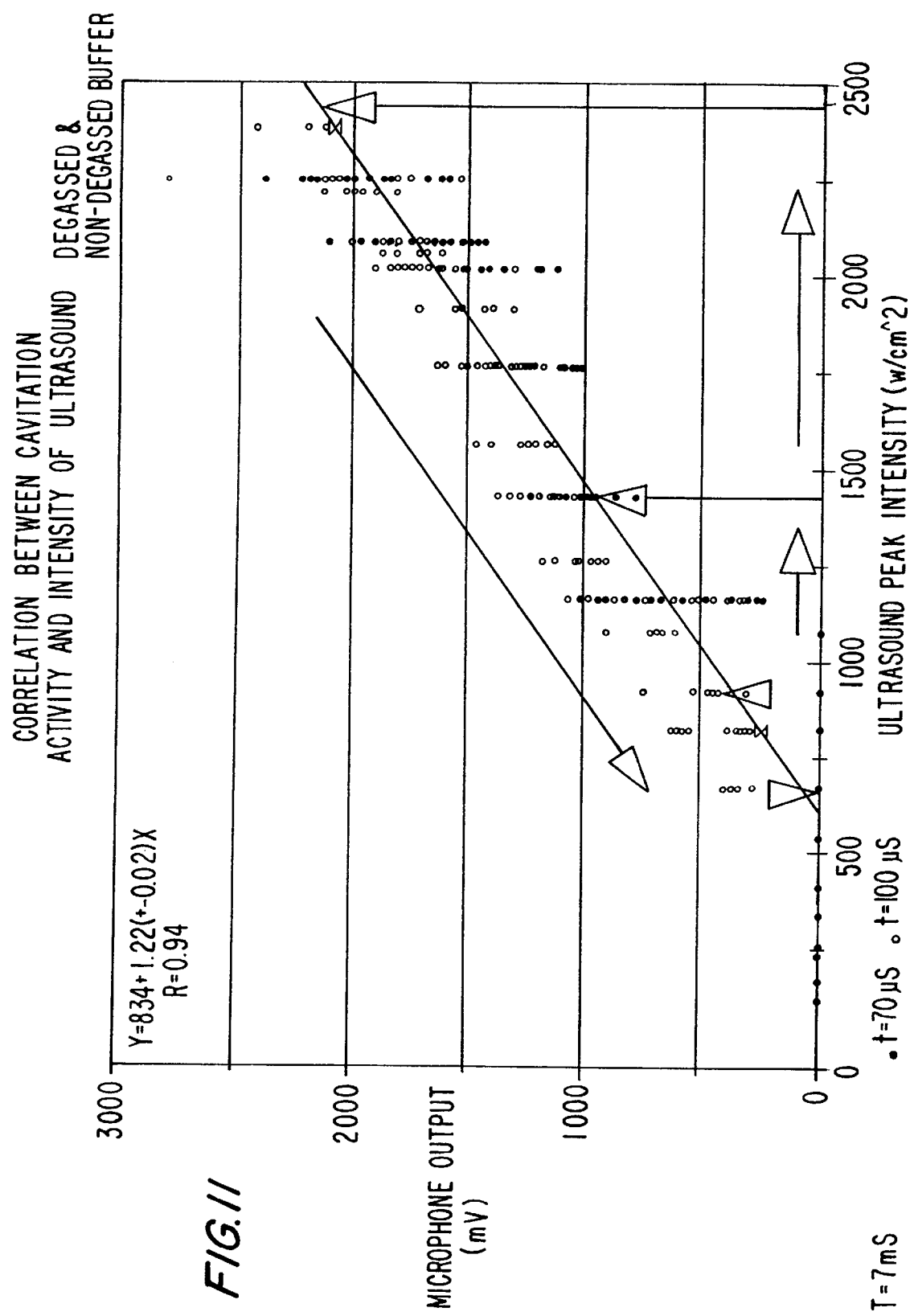

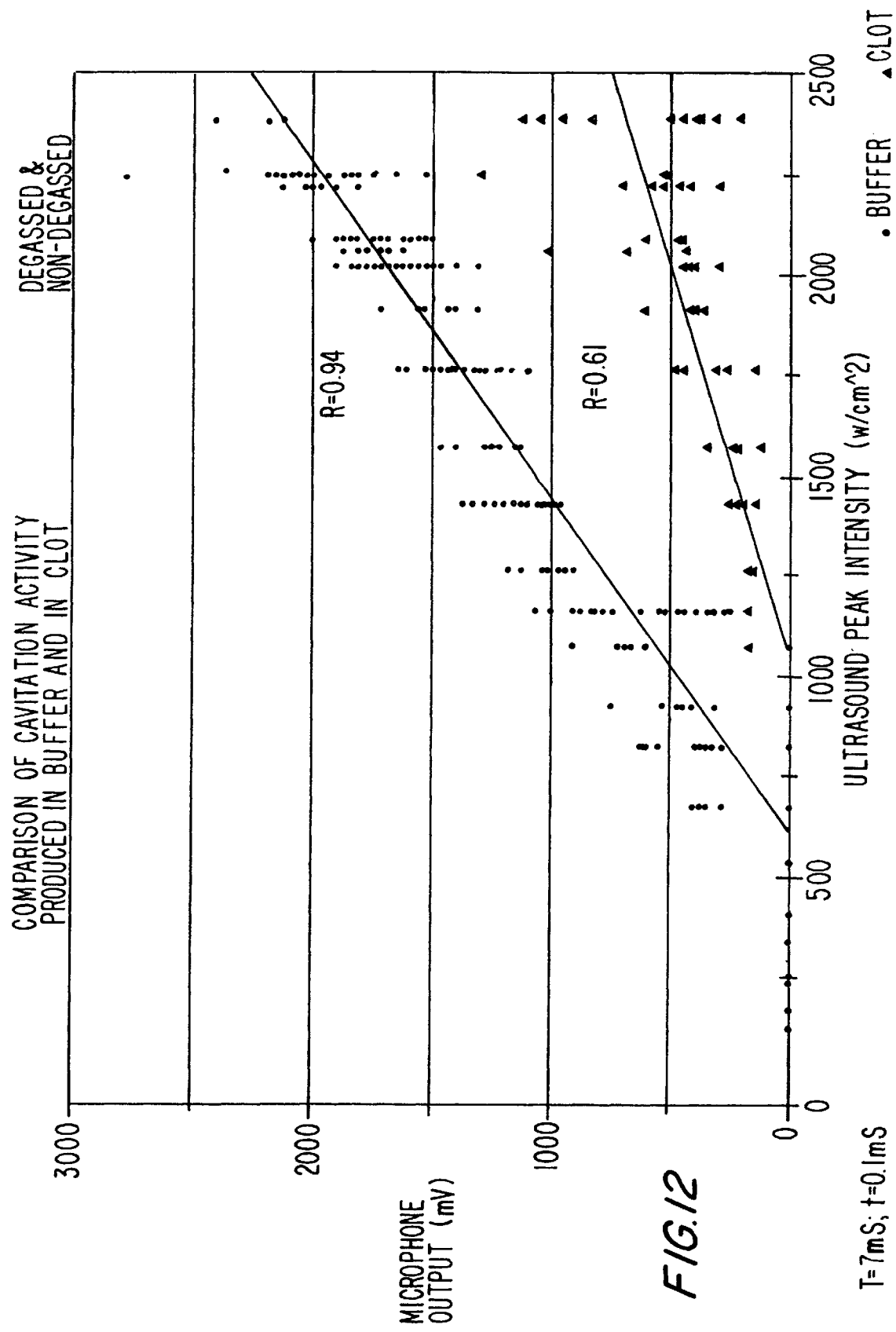

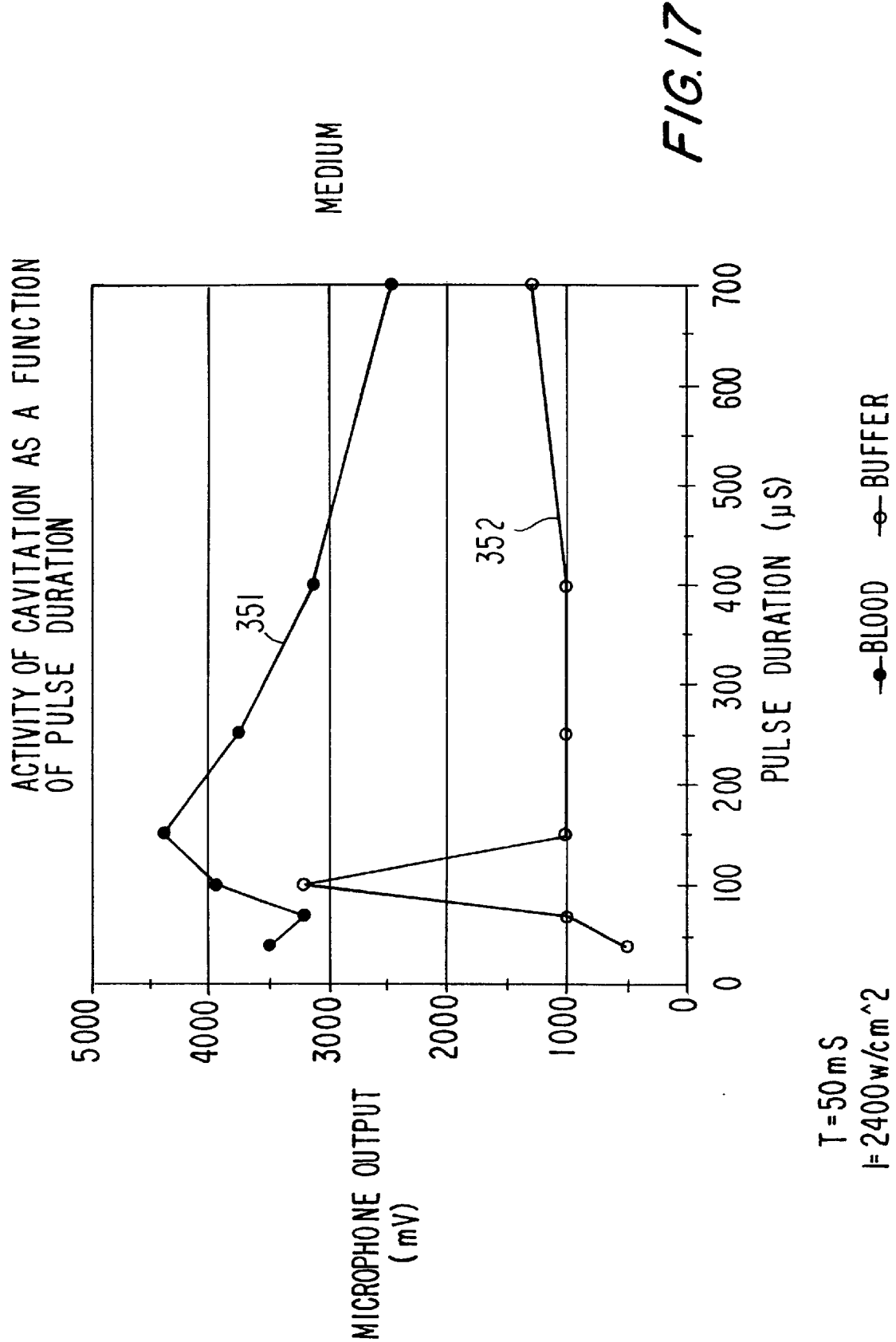

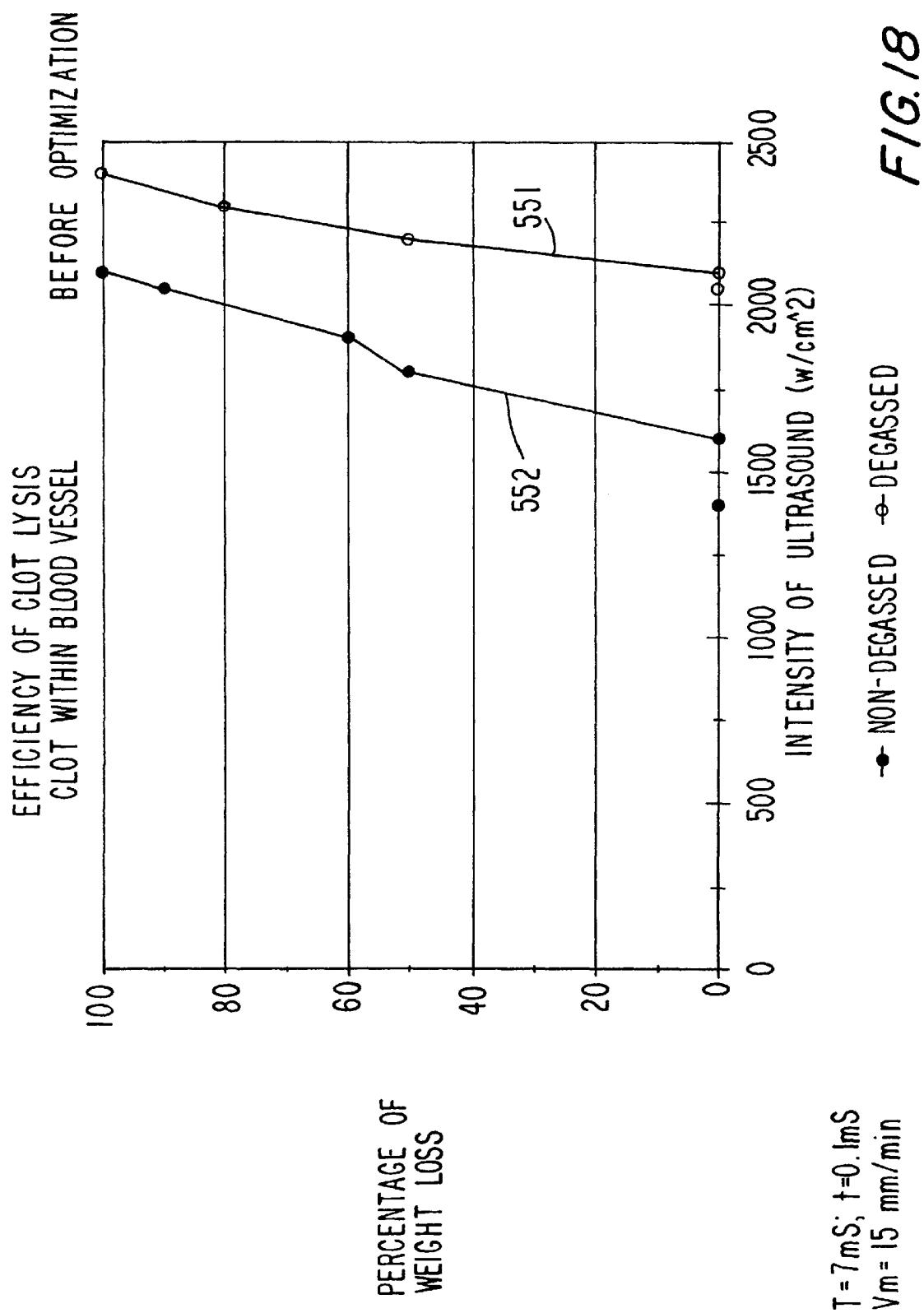

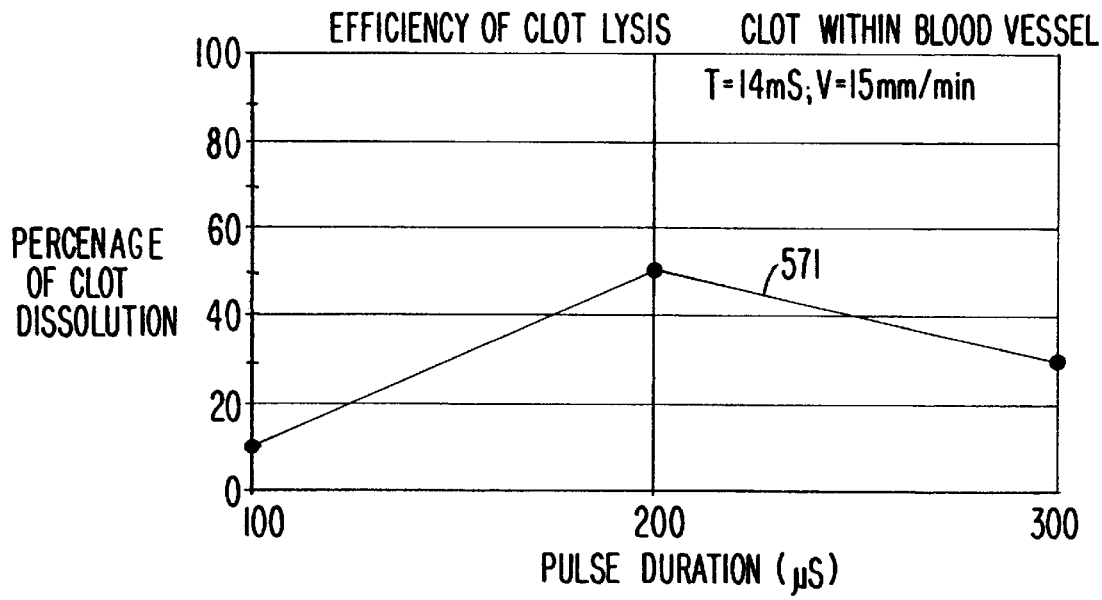
FIG. 20A SEARCH FOR OPTIMUM TIME PARAMETERS OF PULSED MODE SONIFICATION
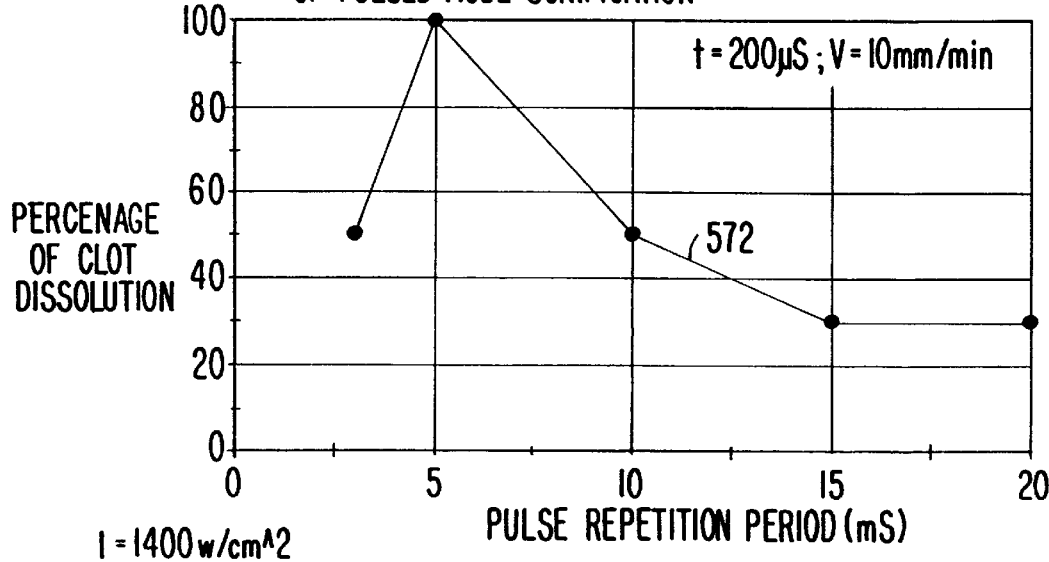
FIG. 20B SEARCH FOR OPTIMUM TIME PARAMETERS OF PULSED MODE SONIFICATION FIG.20C  SEARCH FOR OPTIMUM TIME PARAMETERS OF PULSED MODE SONIFICATION
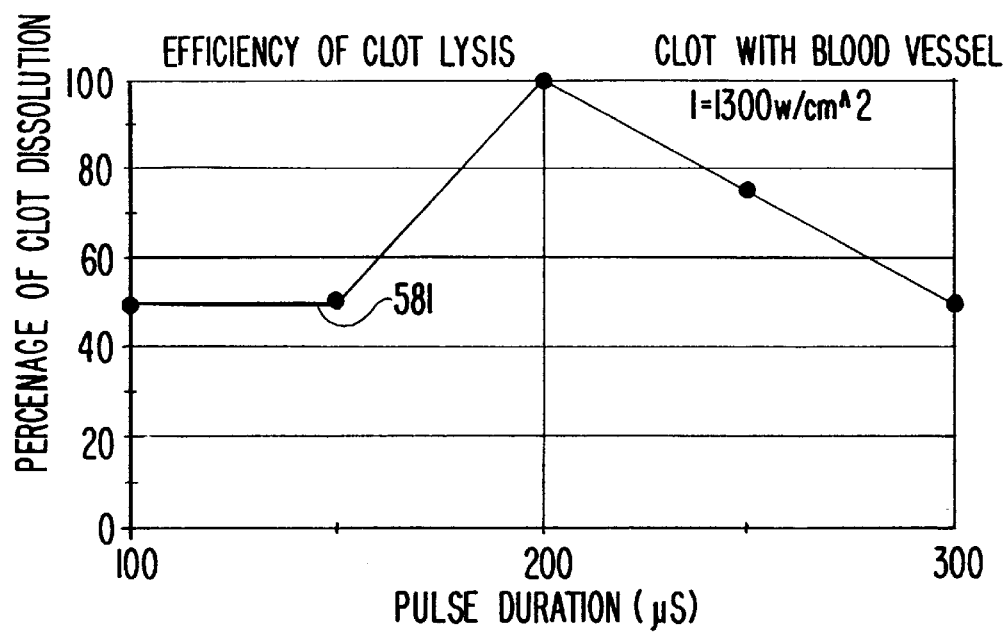
FIG.21  SEARCH FOR OPTIMUM TIME PARAMETERS OF PULSED MODE SONIFICATION
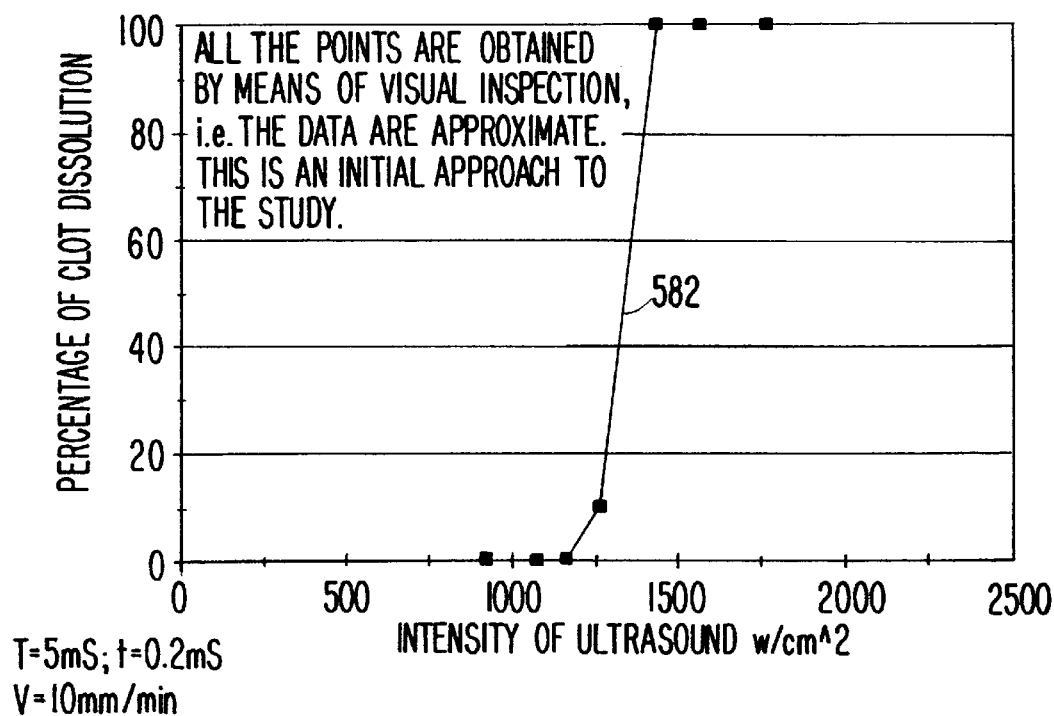

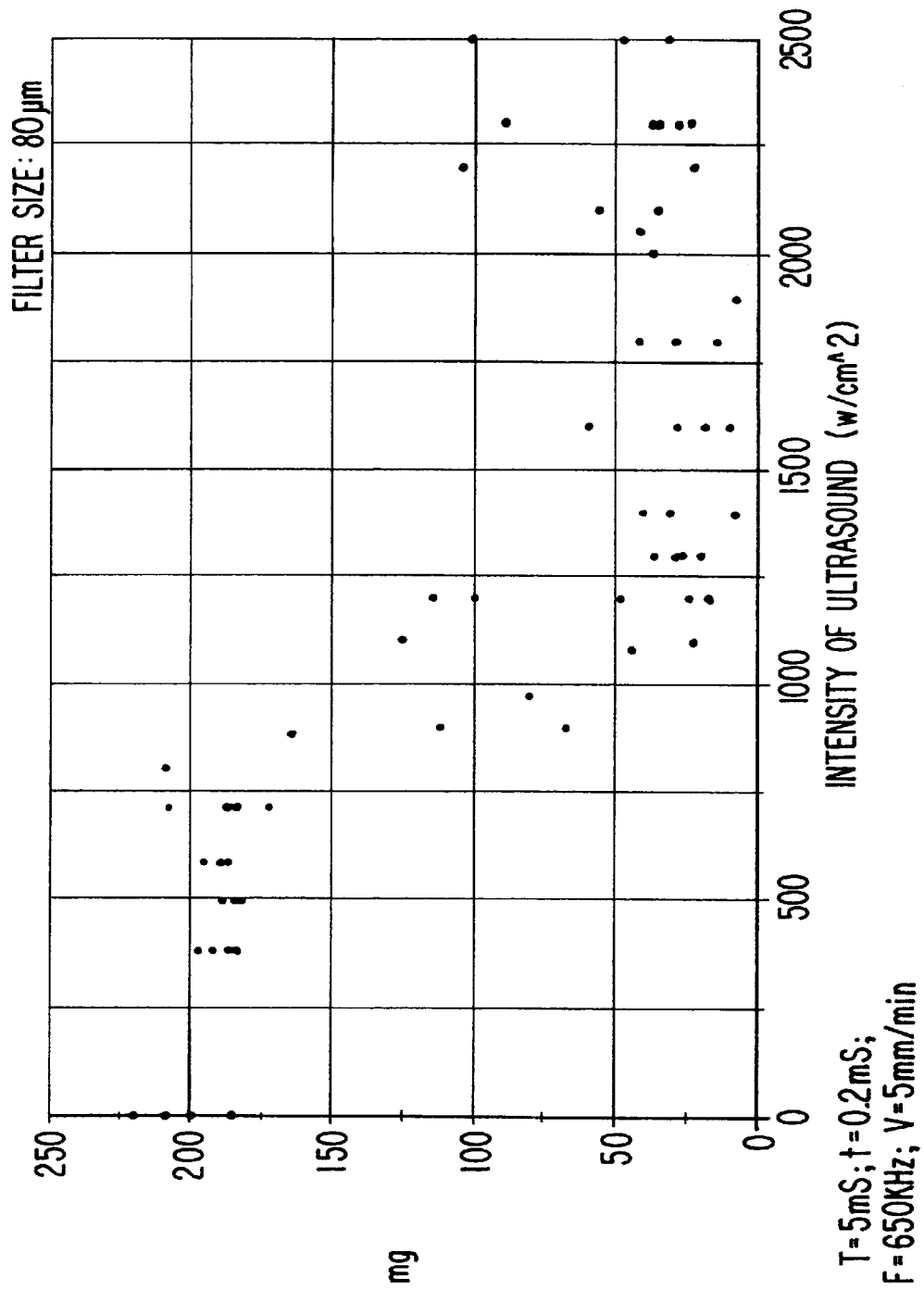

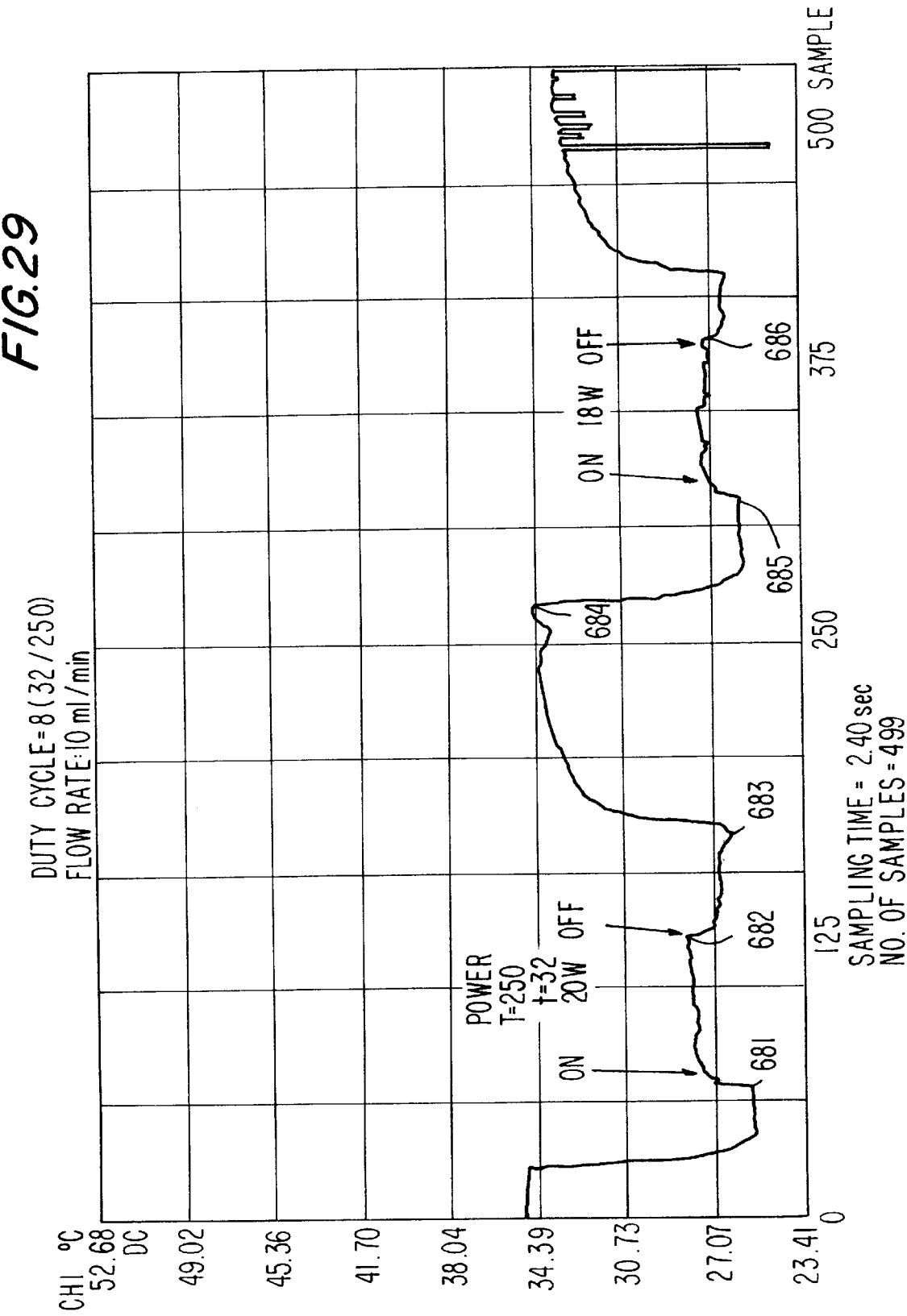

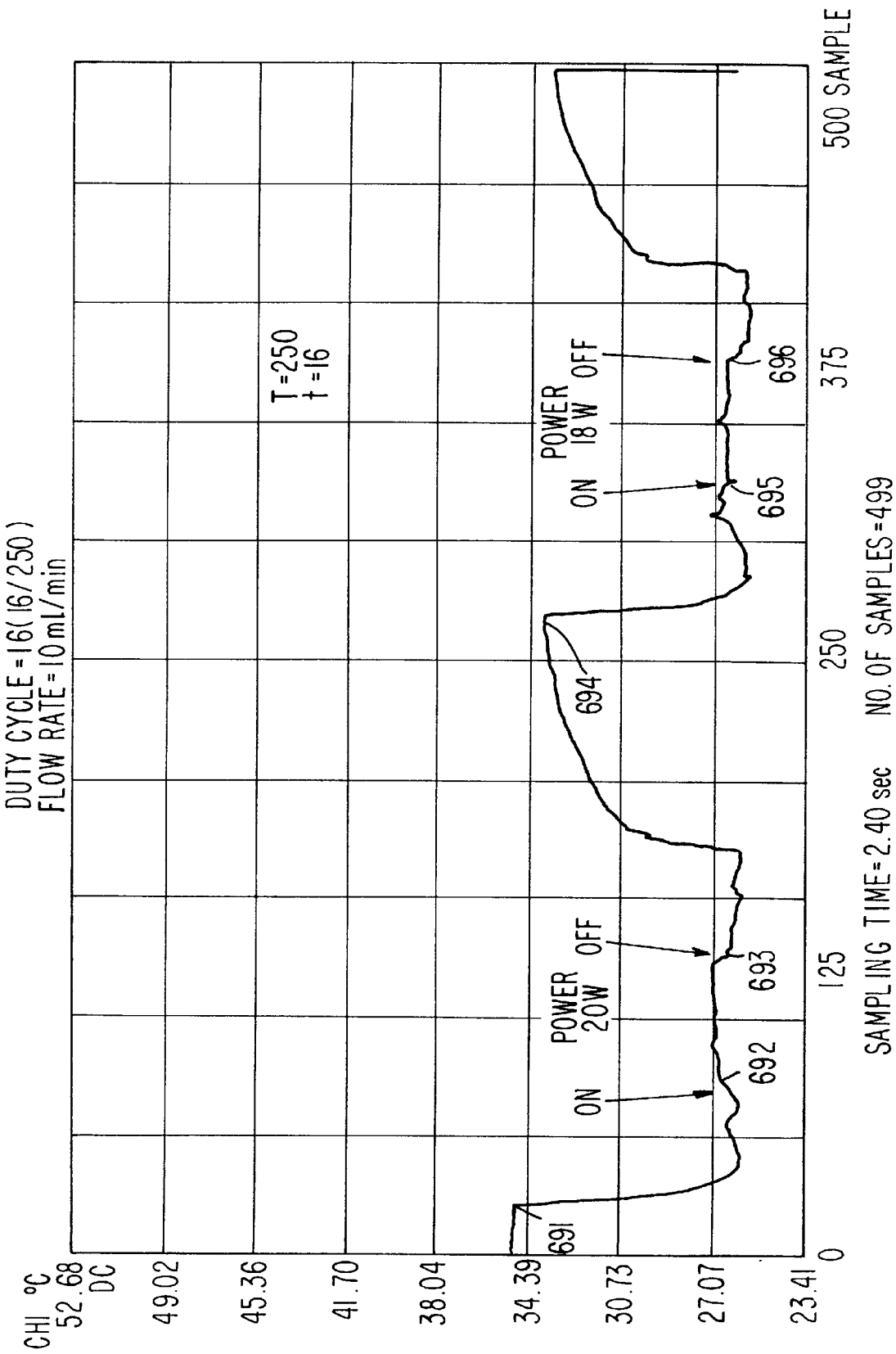

PULSED MODE LYSIS METHOD

BACKGROUND OF THE INVENTION

The invention relates generally to medical devices and more particularly to a method and apparatus for delivering ultrasound energy to a treatment location within a human or other mammal.

The use of ultrasound devices for ablating, lysing or removing material obstructing blood vessels in humans and to otherwise apply ultrasound to locations within the body for therapeutic purposes has been proposed in the art. One such device for removing material obstructing blood vessels is in the form of an elongated ultrasound transmitting probe. This device includes a cavitation generating tip at the distal end of an elongated transmission member. A transducer is used to convert an electrical signal into longitudinal mechanical vibration, which is transmitted to the tip by the transmission member and causes cavitation within the blood vessel to ablate or lyse the obstruction.

One drawback to such a device is the need to insert and advance the device through a blood vessel to the treatment location. This raises various concerns, such as the opportunity for breakage of apparatus parts within the body, injury to the body from the probe itself and so forth. Another drawback is the need to pump cooling fluid down the length of the device. Examples of such devices are discussed in the following patents, applications and publications, the contents of which are incorporated herein by reference: U.S. Pat. No. 5,163,421, issued Nov. 17, 1992; U.S. Pat. No. 5,269,297, issued Dec. 14, 1993; U.S. Pat. Nos. 5,324,255; 4,474,180; Ser. No. 08/858,247, filed May 19, 1997 and Julian Frederick, "Ultrasonic Engineering", John Wiley and Sons (1965). However, it is desirable to provide an improved system and method which overcome drawbacks of these conventional devices and methods.

The non-invasive use of ultrasound has also been proposed. For example, U.S. Pat. No. 5,524,620 dated Jun. 11, 1996, the contents of which are incorporated herein by reference, describes a non-invasive apparatus and method in which focused acoustic energy is used to ablate a thrombus without the need for invasive devices or drugs. However, non-invasive ultrasound systems can exhibit insufficiently satisfactory results. For example, high power is generally needed to cause adequate lysis. This high power is potentially dangerous and thus, it is desirable to operate a non-invasive system more efficiently, at lower average power, in order to provide a greater margin of safety. The effects of non-invasive ultrasound devices on various locations within the body can also be difficult to predict.

Accordingly, it is desirable to provide an improved system and method for the non-invasive application of ultrasound which overcomes inadequacies of the prior art.

SUMMARY OF THE INVENTION

Generally speaking, in accordance with the invention, an apparatus and method for the application of ultrasound to a location within the body is provided. The apparatus can advantageously operate at a pulse duration below about 100 milliseconds and in the range 0.1 milliseconds to 100 milliseconds and a pulse repetition period below about 1 second and in the range of 1 millisecond to 1 second. Duty cycle ratios over 5 and preferably over 8 are also advantageous. Therapeutic applications of ultrasound such as for assisting in the treatment of medical conditions such as cancer and/or other ailments are also provided.

Accordingly, it is an object of the invention to provide an improved apparatus and method for treating locations within the body with ultrasound.

A further object of the invention is to provide a method and apparatus for determining ultrasound application parameters.

Yet another object of the invention is to provide an apparatus and method for therapeutic applications of ultrasound.

Still other objects and advantages of the invention will in part be obvious and will in part be apparent from the specification and drawings.

The invention accordingly comprises the several steps and the relation of one or more of such steps with respect to each of the others, and the apparatus embodying features of construction, combinations of elements and arrangements of pats which are adapted to effect such steps, all as exemplified in the following detailed disclosure, and the scope of the invention will be indicated in the claims.

BRIEF DESCRIPTION OF THE DRAWINGS

For a fuller understanding of the invention, reference is had to the following description taken in connection with the accompanying drawings, in which:

FIG. 9 is a graph showing rate of clot mass dissolution as a function of intensity at the focal area;

FIGS. 11 and 12 are graphs showing microphone output voltage as a function of ultrasound peak intensity in a buffer solution and in a clot, showing that ultrasound initiated randomly, but that once initiated, it could be maintained at decreased intensities and that the threshold and slope are different for the buffer and clot;

FIG. 17 is a graph showing microphone output, which is related to cavitation activity, as a function of pulse duration in both a blood and a buffer solution;

FIG. 18 is a graph showing percentage of weight loss of a clot as a function of ultrasound intensity for a non-degassed and degassed sample, showing a lower intensity threshold and lower intensity requirement for the non-degassed system;

FIGS. 20A, 20B and 20C are three graphs showing percentage of clot dissolution as a function of pulse duration ($\tau$), pulse repetition period (T), and pulse duration ($\tau$), respectively, at intensities of 1400 W/cm$^2$, 1400 W/cm$^2$ and 1300 W/cm$^2$ respectively and shows that optimal parameters can be intensity independent;

FIG. 21 is a graph showing percentage of clot dissolution as a function of ultrasound intensity, manifesting threshold for clot lysis;

FIG. 22 is a graph showing the weight of unlysed clot as a function of ultrasound intensity, manifesting a threshold for clot lysis;

FIGS. 28–30 show ultrasound probe temperature in activated and unactivated states, both with and without the use of cooling fluid, in a continuous wave mode of probe operation, and in duty cycles of 8.

DESCRIPTION OF PREFERRED EMBODIMENTS

Significant therapeutic effects can be achieved by applying ultrasound to locations within a living body. Generally, a transducer converts an electrical signal to mechanical vibration, which causes the propagation of ultrasound waves through some medium or media. If these waves are of sufficient intensity, they create cavitation within a medium at a desired location as micro bubbles are formed and collapse. This generates extraordinarily high activity at the cavitation site.

A transducer can be operated in a continuous mode or in a pulsed mode. In a continuous mode, the signal to the transducer is always causing the transducer to generate sufficient vibration to maintain cavitation at the desired location. In a "pulse" mode, the signal amplitude is reduced sufficiently (or eliminated) to permit cavitation to pause between pulses of high amplitude during which cavitation occurs. Certain conventional pulsing methods apply ultrasound in one to several second doses, followed by pauses of approximately equal duration or even durations longer than the duration of the activating signal. This is conventionally performed to permit objects which became hot during the activation process to cool down. It has been discovered that applying ultrasound in an improved pulsed mode can provide substantial advantages, compared to conventional pulsing modes of operation.

Figure 1A:
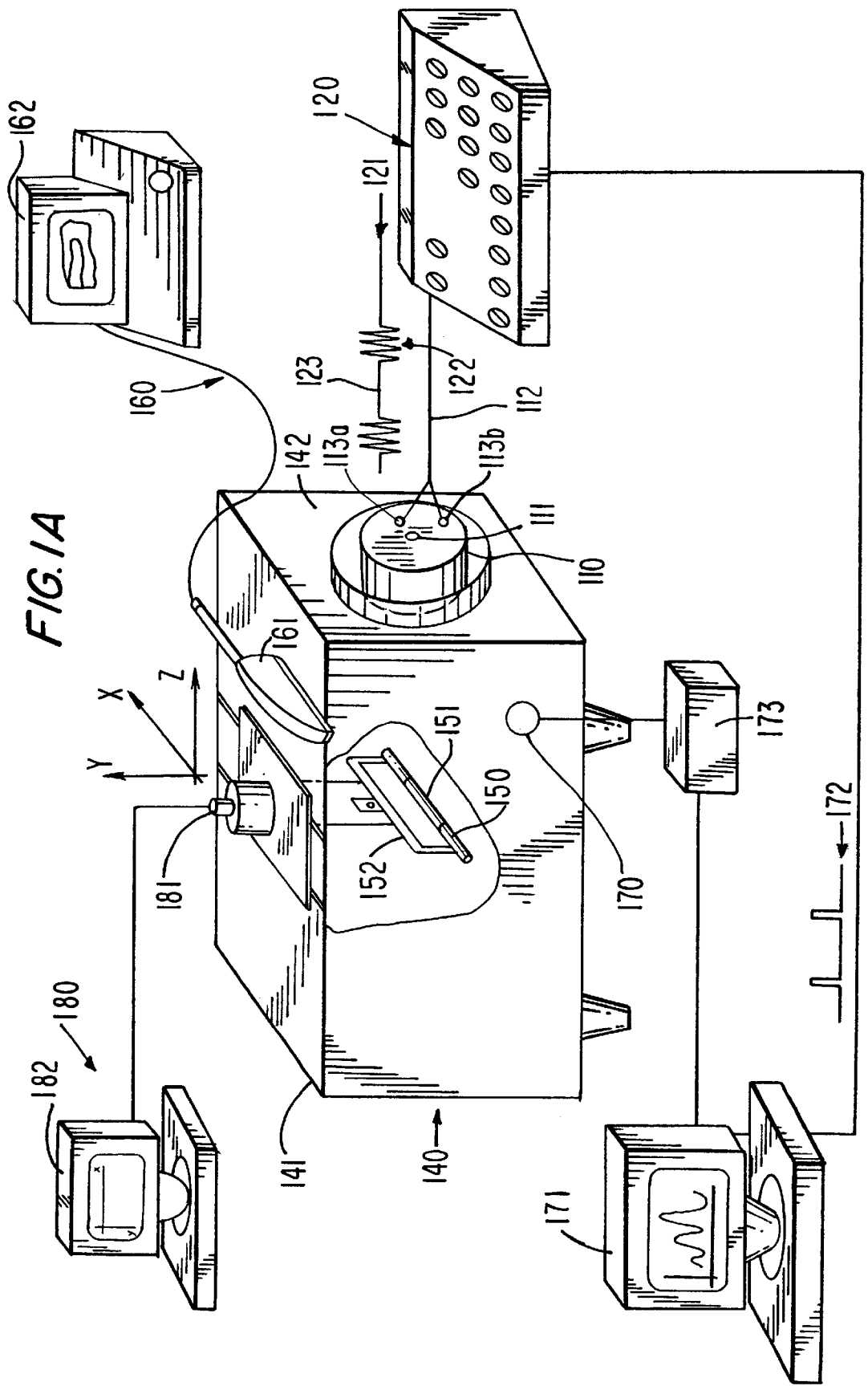
FIG. 1A is a schematic perspective view of a system for the non-invasive use and testing of ultrasound energy.
Figure 1B:
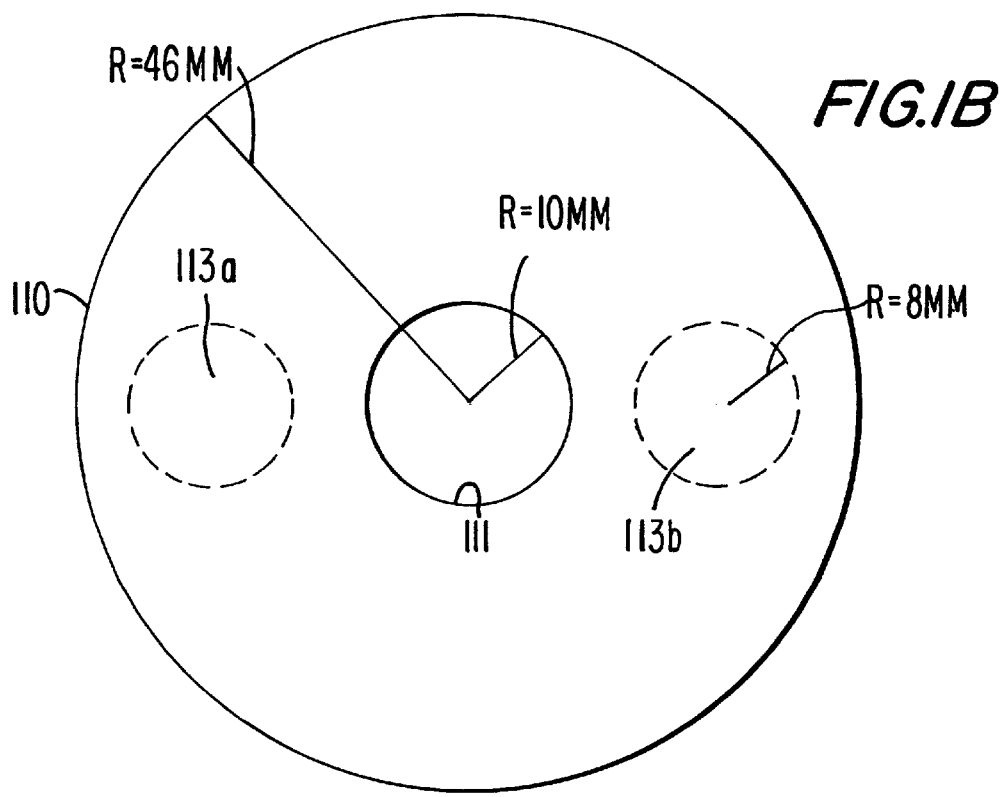
FIG. 1B and 1C are front and side views of the transducer shown in FIG 1A.
Figure 1C:
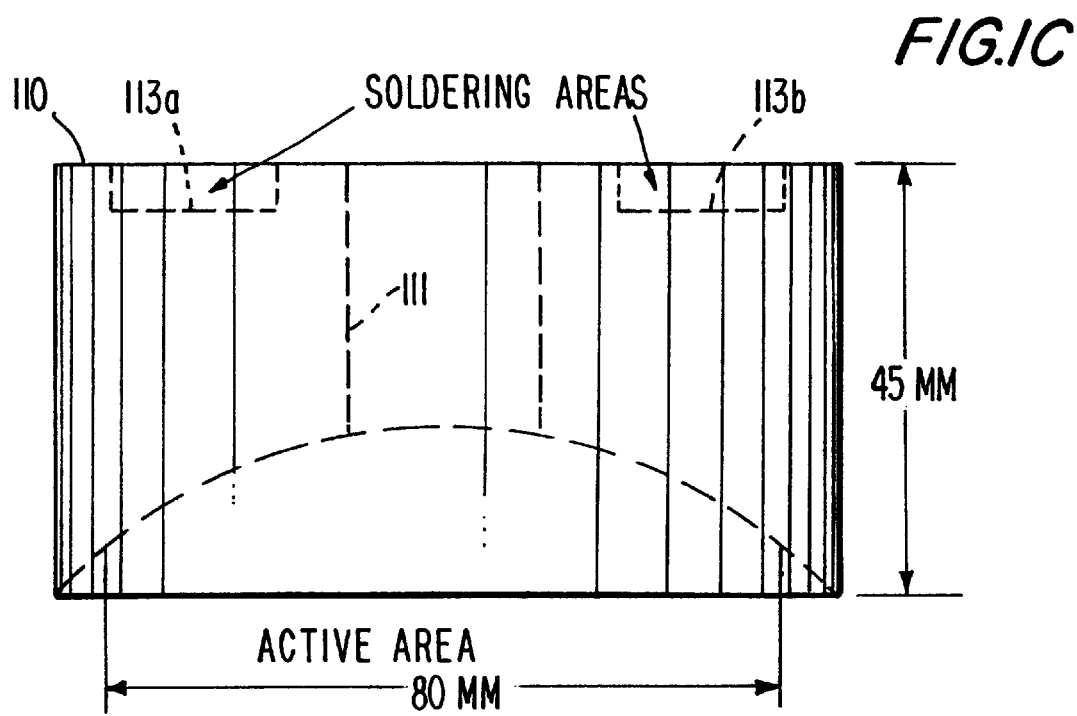

Referring to FIG. 1A, an example of a system for providing the non-invasive application of ultrasound to a test sample in a model representing a body part, which can be readily modified to apply ultrasound to a location within a living body, is shown generally as non-invasive ultrasound application system 100. Non-invasive ultrasound system 100 includes a therapeutic focused ultrasound transducer 110, which is activated by an electrical signal from a signal generator 120. Therapeutic transducer 110 can be constructed to operate at up to 750 KHz and can be formed with a 1–3 ceramic composite. A 1–3 composite transducer includes rods of PZT inserted into a polymer support and has very high energy transfer efficiency. Front and side views of one embodiment of transducer 110 are shown in FIGS. 1B and 1C. Therapeutic transducer 110 includes a hole 111 at the center thereof. Hole 111 permits the use of an optional ultrasound imaging probe (not shown) which can guide and monitor the therapy with ultrasound during application. One example of a suitable transducer, which was used in experiments presented herein, is about 45 mm thick, has an overall radius of 46 mm, a central active area with a radius of 40 mm and a central bore with a radius of about 10 mm. Electrical connections are on either side of the central bore at disk shaped depressions having an 8 mm radius. Alternative transducers can be substituted.

To operate transducer 110, generator 120 sends a signal 121 through a pair of electric wires 112, which are coupled to transducer 110 at attachment points 113$a$ and 113$b$. Signal 121 is formed with a plurality of energy pulses 122 of duration $\tau$ at an amplitude (A) and a frequency (f). As used herein, a pulse will be considered the "on" portion 122 of signal 121, which is of sufficient amplitude to maintain cavitation and is followed by an "off" section 123 of signal 121 of insufficient amplitude to maintain cavitation. The duration of time between the beginning of successive pulses 122 is referred to as pulse repetition period T. It has been determined that pulse duration $\tau$ is advantageously significantly smaller than pulse repetition period T.

To model the effects ultrasound emitted from therapeutic transducer 110 would have on a location within a living body, a model system 140 was constructed. Model system 140 includes an open Plexiglas water tank 141 with a hole in a front side 142 for inserting therapeutic transducer 110. Tank 141 was filled with water, which was either degassed or non-degassed, depending on the particular experiment to be run. When water was not degassed, it included small air bubbles which served as a nuclei for cavitation initiation. Decreasing the number of bubbles in the water increases the energy needed to initiate cavitation.

To obtain information about the focal region of ultrasound emitted from transducer 110, a hydrophone (not shown) was positioned at various locations within a dedicated tank. It was found that when activated by generator 120 at low intensities below the cavitation threshold, transducer 110 creates an acoustic field with a focal region having an elongated ellipsoid or cigar shape.

To obtain information regarding the effects of ultrasound on clots within a living body, a bovine vessel 150 having a clot 151 therein or a clot attached to the front of a bovine vessel wall was suspended within tank 141 by a specimen holder 152. Depending on the experiment to be run, vessel 150 was filled with either blood or a buffer solution. The vessel 150 and the clot 151 were moved by a computerized x-y positioning a system 180 through a mounting 181 and a computer controller 182. Certain information regarding the effects of applied ultrasound were compiled with an ultrasound imaging device 160, formed with an imaging ultrasound transducer 161, coupled to a processor 162 for interpreting information received from transducer 161 and displaying an image thereof. Additional information was compiled through the use of a microphone 170 attached to tank 141, coupled to a frequency analyzer 171 through an amplifier 173, which also receives a trigger signal 172 from generator 120. Trigger signal 172 corresponds to transducer activation signal 121, so that only sound transmitted from microphone 170 when transducer 110 is activated will be analyzed.

It was determined that advantageous benefits can be achieved when ultrasound is applied at a pulse duration $\tau$ not greater than about 100 milliseconds (msec). A range of about 0.01 to 100 milliseconds is preferred. Also, pulse repetition periods T below about 1 second are preferred, as are pulse repetition periods in the range 1 millisecond to 1 second. Duty ratios $T/\tau \geq$ about 5, and preferably $\leq 8$ are preferred.

Non-invasive therapeutic ultrasound can be practiced at a frequency of about 100 to 1000 KHz and far broader. Invasive-type (probe-based) therapeutic ultrasound can be practiced at a frequency range of 20 to 100 KHz and far broader. At a frequency of preferably 100 to 1000 KHz advantageous operating parameter include T=about 1 to 100 milliseconds, preferably about 2.5 to 90 milliseconds and more preferably 2.5 to 75 milliseconds and/or $\tau$=0.01 to 2.0 milliseconds, preferably 0.02 to 1.1 milliseconds and more preferably 0.1 to 0.3 milliseconds. These parameters are particularly well suited for a non-invasive-type device, particularly one applying ultrasound at $I \geq$ about 750 W/cm$^2$, more preferably $\leq$ about 1000 W/cm$^2$.

At a frequency range preferably of 20 to 100 KHz, advantageous operating parameters include $T \leq$ about 1000 milliseconds preferably $\leq$ about 600 milliseconds, more preferably about 100 to 500 milliseconds and/or $\tau \leq$ about 100 milliseconds, preferably about 10 to 100 milliseconds, more preferably 20 to 60 milliseconds. These parameters are particularly well suited for use with an invasive-type device, especially one operated at a peak power output of over 10 watts, such as one operated at 10–40 watts, preferably 15–30 watts. When pulse parameters are correctly selected, an invasive-type probe can be operated with substantially no cooling fluid.

The following examples illustrating the non-invasive application of ultrasound were conducted in a water tank with a system having the general construction shown in FIG. 1A. These examples are provided for purpose of illustration only, and are not intended to be construed in a limiting sense.

EXAMPLE 1

Figure 2:
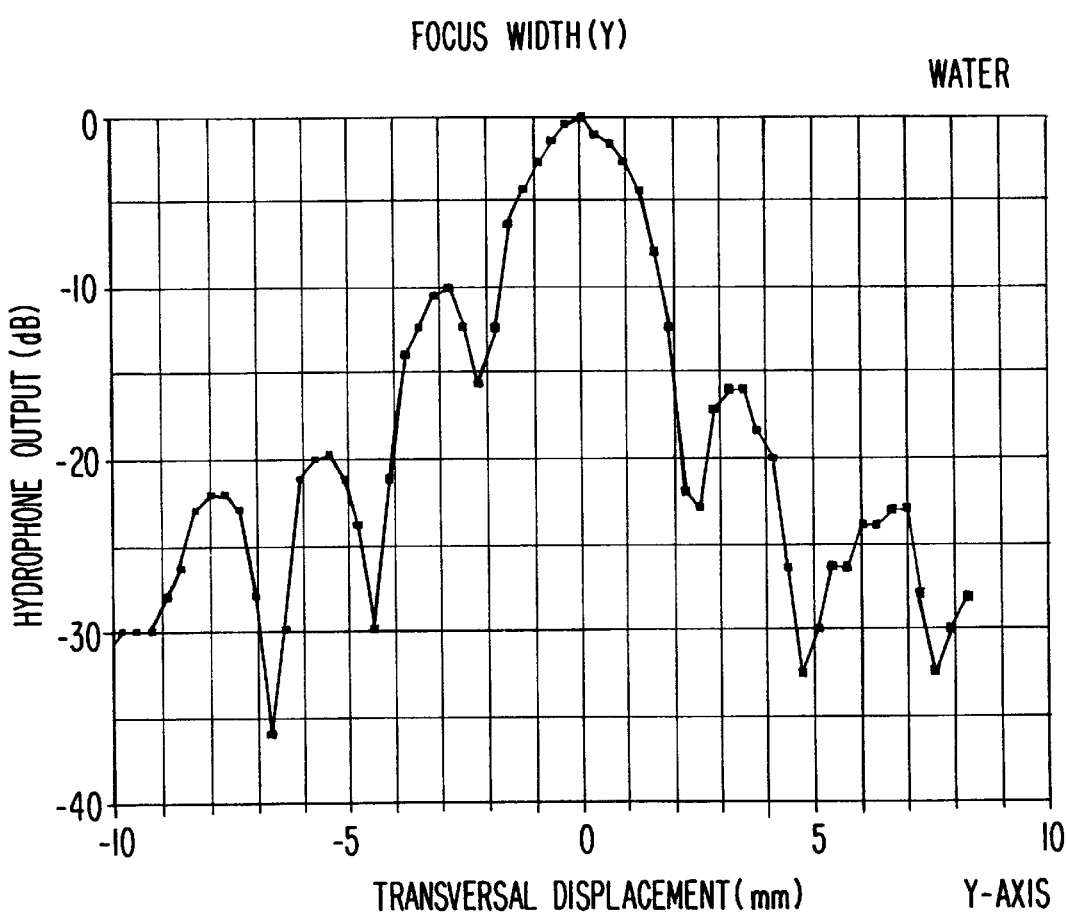
FIG. 2 is a graph showing hydrophone output, in decibels, as a function of transversal displacement of the hydrophone along the Y axis to establish the focal width of ultrasound in the Y direction.

The transducer was operated at a frequency of 750 KHz, at a pulse duration of $\tau$=20 $\mu$s, a pulse repetition period of T=74 ms and a potential of 46 V. The hydrophone output was measured in decibels as a function of transversal displacement in mm along the Y axis, parallel to the transducer plane and corresponded to the predicted cigar shape at a distance of 5 cm from the transducer. The results are shown in FIG. 2.

EXAMPLE 2

Figure 3:
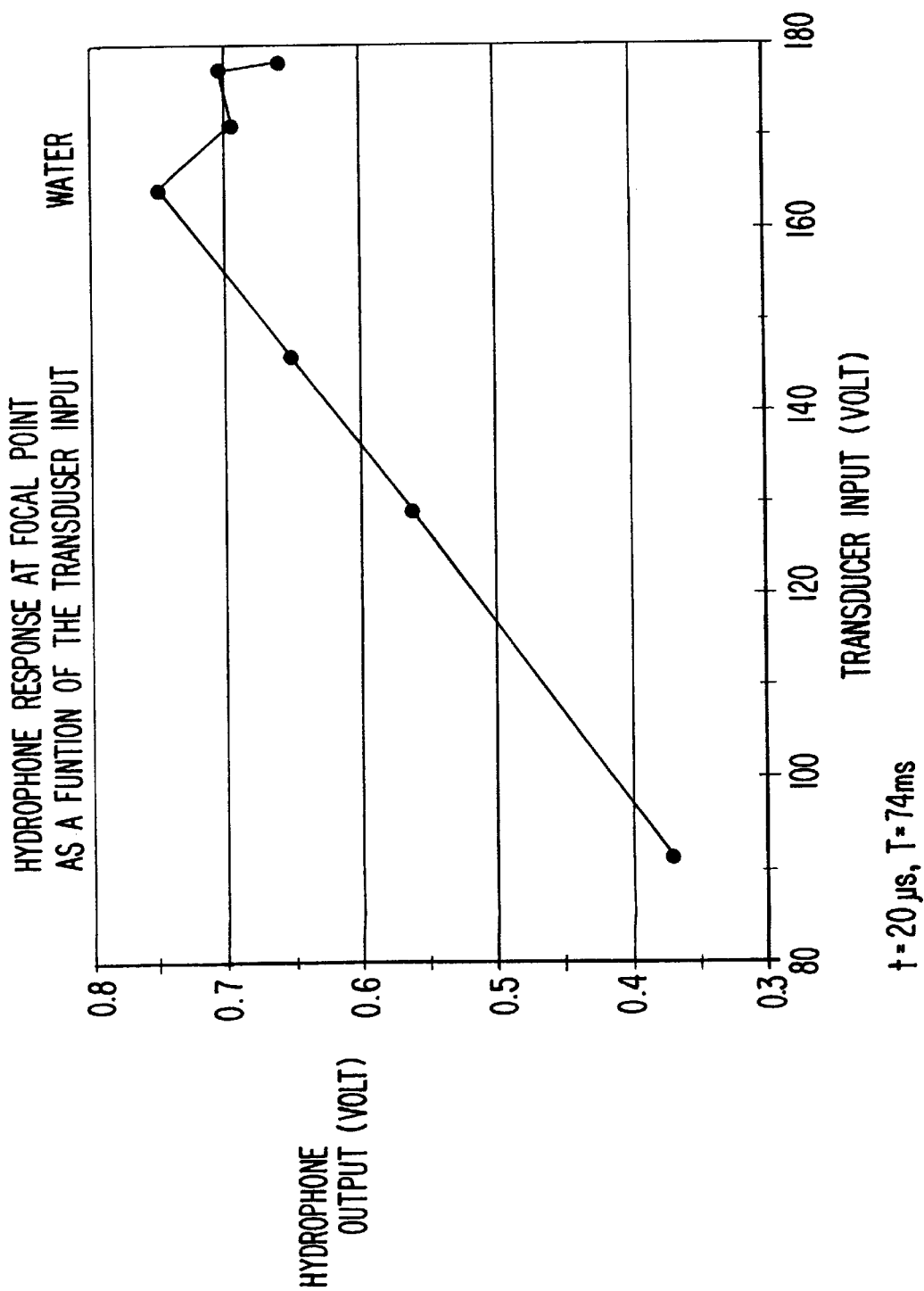
FIG. 3 is a graph showing hydrophone output voltage as a function of transducer input voltage, showing that electric potential above 160 volts, and therefore increased wattage, caused a decrease in hydrophone output as a result of exceeding the cavitation threshold of the medium.

The hydrophone response at the focal point both above and below the cavitation threshold was measured. Referring to FIG. 3, it can be seen that when $\tau$=20 $\mu$s and T=74 ms and transducer input was increased above about 160 volts, the effects of cavitation can be determined by a decrease in hydrophone response at the focal point, as energy is absorbed before the focal point, leading to a decrease of sound energy at the focal point itself.

EXAMPLE 3

Figure 4:
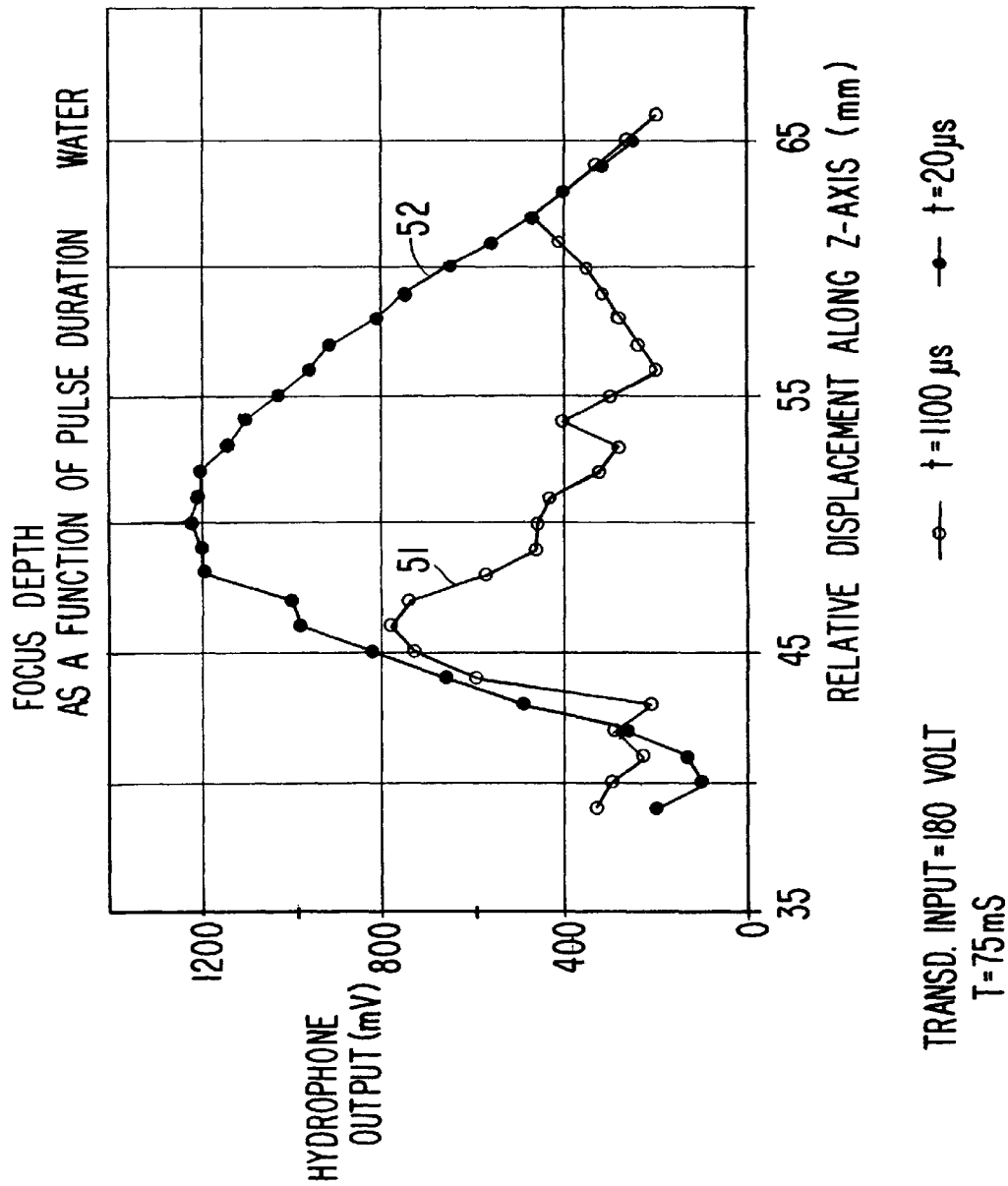
FIG. 4 is a graph showing hydrophone output voltage as a function of displacement of the transducer along the Z-axis for both short duration pulses and relatively longer duration pulses, showing that a longer pulse duration ($\tau$) can initiate cavitation.

The effects of pulse duration on cavitation were measured by operating the transducer at an input potential of 180 V, T=75 ms and measuring hydrophone output in a water filled tank at $\tau$=1100 $\mu$s (curve 51 in FIG. 4) and 20 $\mu$s (curve 52 in FIG. 4). As shown in FIG. 4, the longer pulse duration led to cavitation, whereas the shorter pulse duration exhibited no breakdown in focal depth. Accordingly, the initiation of cavitation depends not only on input voltage as has been believed, but also on pulse duration.

EXAMPLE 4

Figure 5:
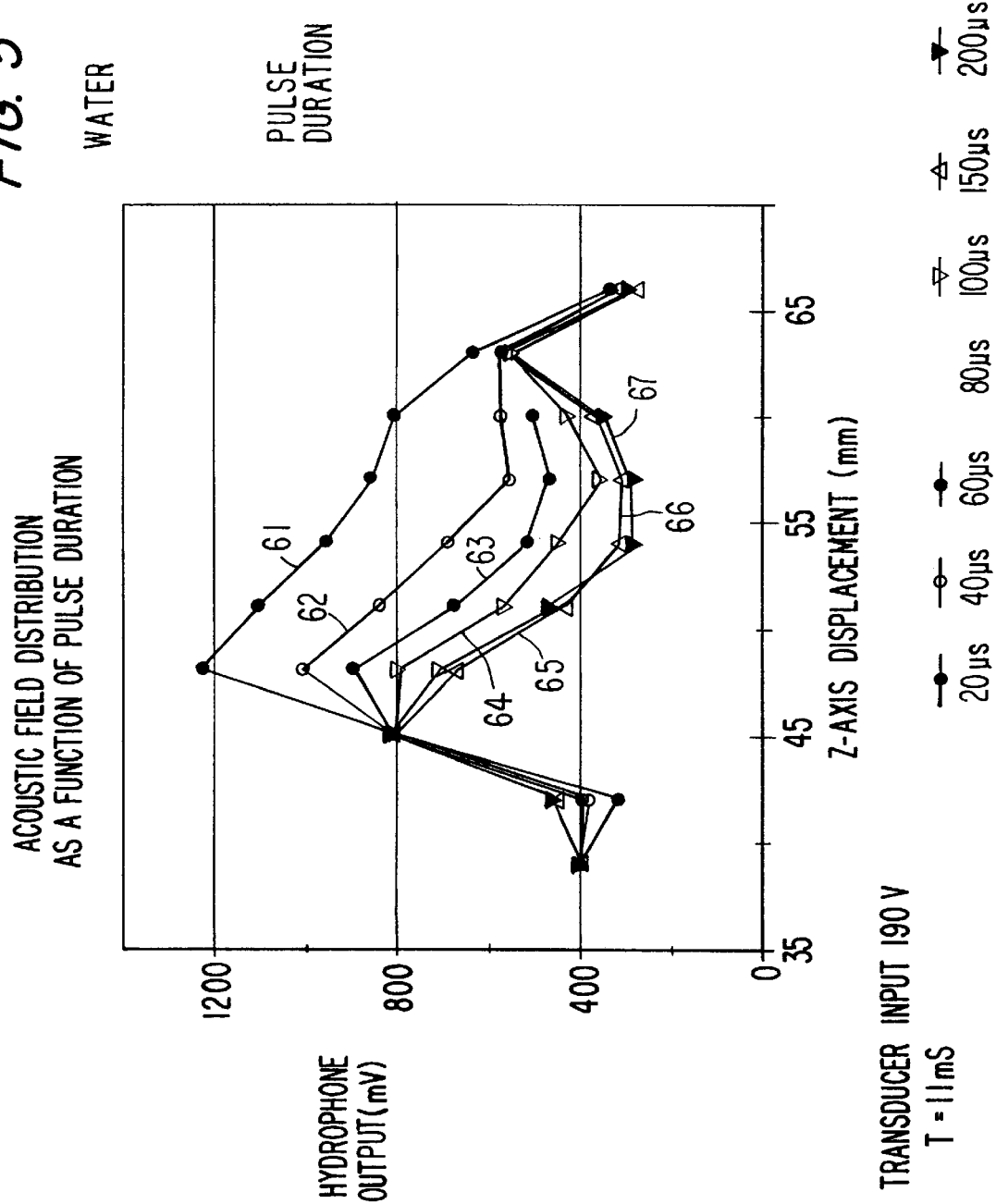
FIG. 5 is a graph showing hydrophone output voltage as a function of Z-axis displacement for various pulse durations, showing that longer pulse durations were associated with larger decreases in acoustic amplitude after exceeding the cavitation threshold.

The effects of pulse duration on cavitation were also analyzed for seven different pulse durations at 190 V and T=11 ms. Referring to FIG. 5, curve 61 is from a duration of 20 $\mu$s, curve 62 is from a duration of 40 $\mu$s, curve 63 is from a duration of 60 $\mu$s, curve 64 is from a duration of 80 $\mu$s, curve 65 is from a duration of 100 $\mu$s, curve 66 is from a duration of 150 $\mu$s and curve 67 is from a duration of 200 $\mu$s. Longer pulse durations were shown to be directly proportional to larger decreases in hydrophone output and consequentially, increased cavitation activity.

EXAMPLE 5

Figure 6:
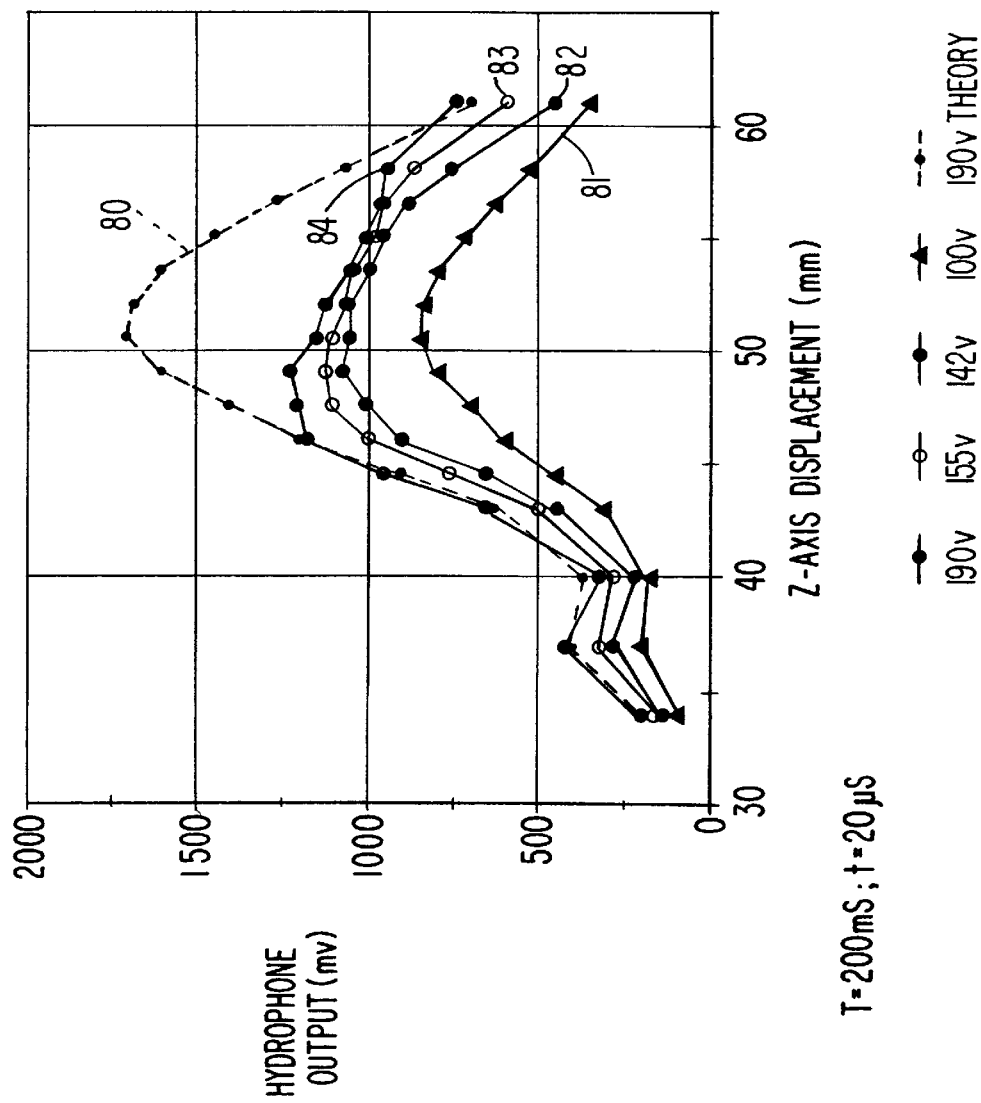
FIG. 6 is a graph showing hydrophone output voltage as a function of Z-axis displacement for transducer inputs of varying voltage, showing that cavitation was evidenced by a decrease in actual hydrophone output from the theoretical output.

The effects of increased voltage (increased power and intensity) on cavitation were analyzed more fully, by measuring hydrophone output as a function of Z-axis displacement at T=200 ms and $\tau$=20 $\mu$s, at various input voltages. Referring to FIG. 6, curve 80 shows a theoretical plot at 190 volts, if no cavitation had occurred, curve 81 is from 100 volts, curve 82 is from 142 volts, curve 83 is from 155 volts and curve 84 is from 190 volts. Higher electrical input corresponded to higher amplitude and larger decreases in acoustic amplitude, compared to a theoretical prediction and hence, greater cavitation effect.

EXAMPLE 6

Figure 7:
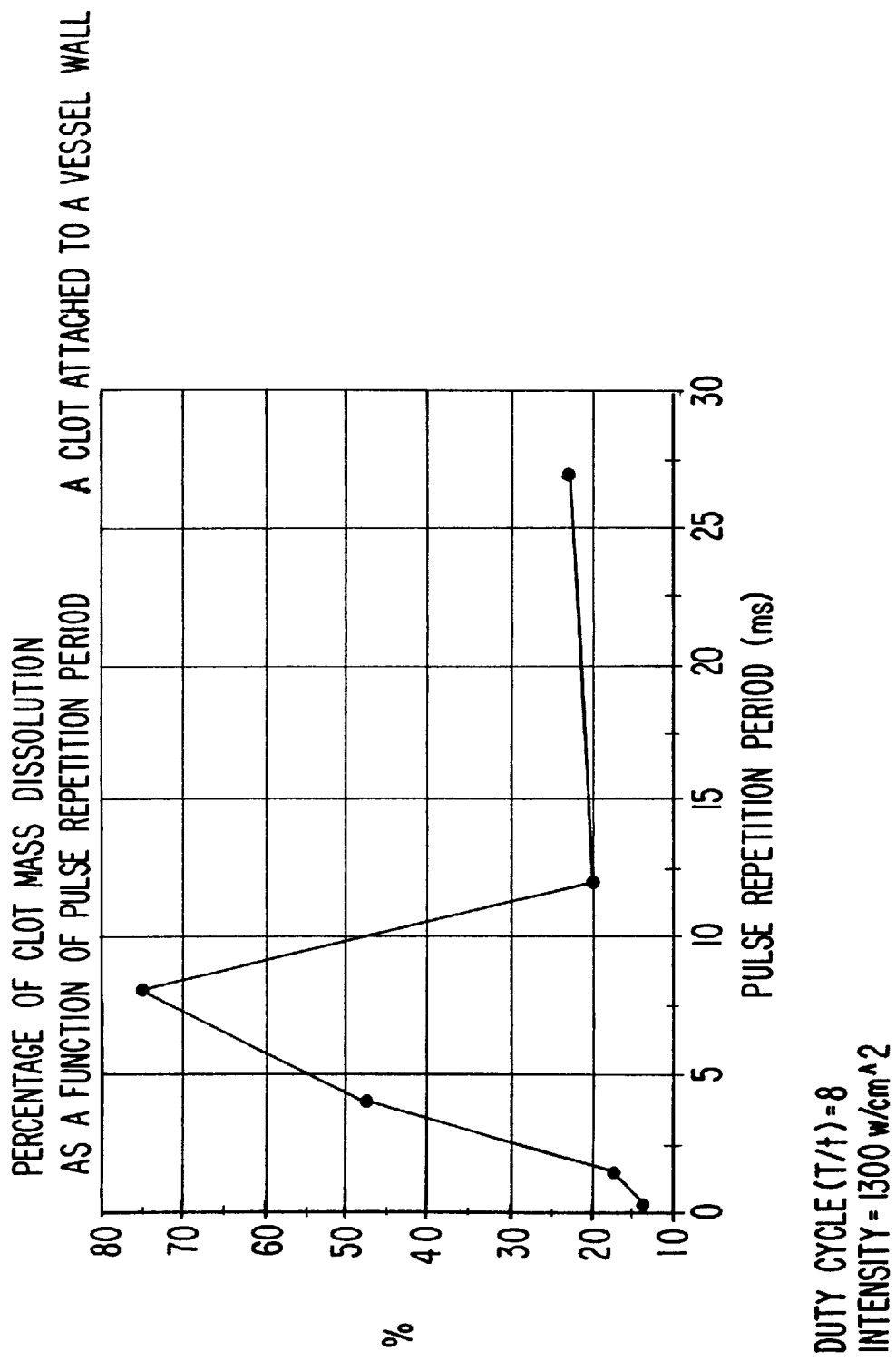
FIG. 7 is a graph showing change in percentage of clot mass dissolution as a function of change in the pulse repetition period (T), showing that an appropriate pulse repetition period has a significant effect on the efficiency of clot lysis.

The apparatus shown in FIG. 1A was used to dissolve a blood clot attached to the front of a wall taken from a bovine blood vessel. Referring to FIG. 7, the transducer was operated at a duty cycle (T/$\tau$)=8 and an intensity of 1300 W/cm$^2$ and the pulse repetition period was varied over a range of about 0.5 to 27 ms. Optimal results were achieved in a range of about T=4 to 10 ms, with peak clot dissolution efficiency at a pulse repetition period of about 8 ms and a pulse duration of about $\tau$=1 ms. Thus, the operating parameters including a duty cycle of about 8 were deemed acceptable.

EXAMPLE 7

Figure 8:
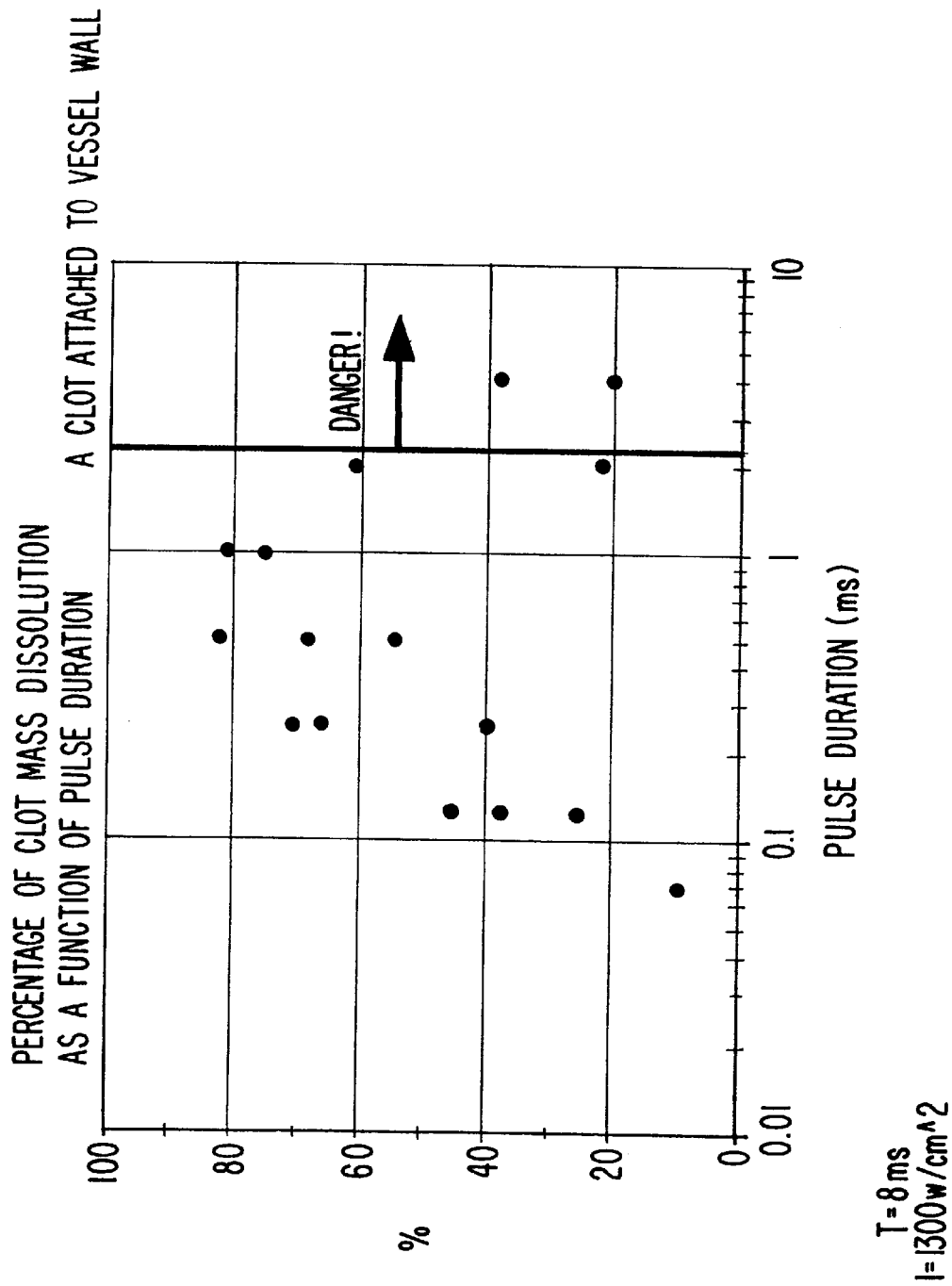
FIG. 8 is a graph showing percentage of clot mass dissolution as a function of pulse duration ($\tau$), showing a strong dependency of clot dissolution and danger to the blood vessel on pulse duration.

The use of non-invasive ultrasound to lyse a clot attached to a vessel wall at parameters of I=1300 W/cm$^2$ and T=8 ms, for pulse durations ranging from about 0.07 ms to about 5 ms were performed and the results are presented in FIG. 8. The results show optimal clot dissolution at pulse durations of about τ=0.5 to 1.0 ms. It was also determined that increasing the pulse duration above about 2.3 ms began damaging the vessel wall. It is believed that lysis is mechanical in nature and depends on various pulse parameters. Damage to the vessel (and to a probe in the case of invasive applications of ultrasound) is related to thermal effects, which are related to the accumulated energy transferred to a volume over time. Thus, by operating at a sufficiently short pulse duration, a clot can be lysed, without building up a dangerously high amount of heat. It appears that operating above the cavitation threshold, but less than about 50% of the pulse duration which can damage the vessel, can be both a safe and effective operating parameter.

EXAMPLE 8

Referring to FIG. 9, the rate of clot mass dissolution as a function of ultrasound intensity at the focal area was analyzed with T=8 ms and τ=1 ms. A non-linear increase in dissolution rate with intensity was observed with fastest dissolution at intensities in the 1200–1400 W/cm$^2$ range.

EXAMPLE 9

The use of an ultrasound imaging system similar to system 160 shown in FIG. 1A provided additional information regarding the use of ultrasound for blood clot lysis. It is possible to visualize the clot during ultrasound application.

A bovine artery segment was filled with non-degassed PBS. The transducer was operated at frequency, f=650 KHz, transducer excitation voltage, $U_{p/p}$=116 volts, T=7 ms and τ0.5 ms. Bright reflection images corresponding to cavitation were seen only at the posterior artery wall. This indicated that the transducer was located too close to the vessel. After the transducer was moved away from the vessel, reflection spots, indicating cavitation within the vessel were observed, indicating proper positioning of the transducer.

After the transducer was moved still farther away, bright reflection corresponding to cavitation was observed only at the anterior artery wall, indicating that the transducer was located too far from the vessel. Thus, by combining conventional imaging ultrasound with non-invasive ultrasound lysis, it is possible to assure that the ultrasound focal point is at a desirable location within the body.

EXAMPLE 10

Figure 10A:
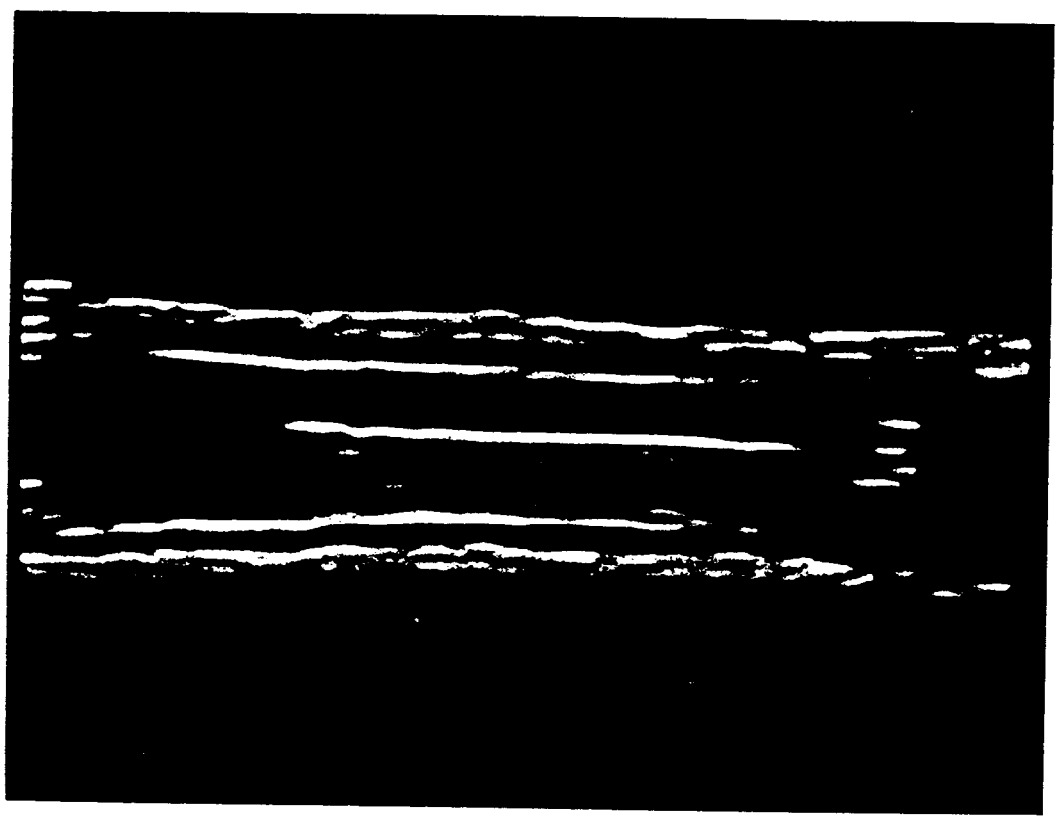
FIGS. 10A and 10B are ultrasound images of a clot within an artery segment, before and after ultrasound treatment.
Figure 10B:
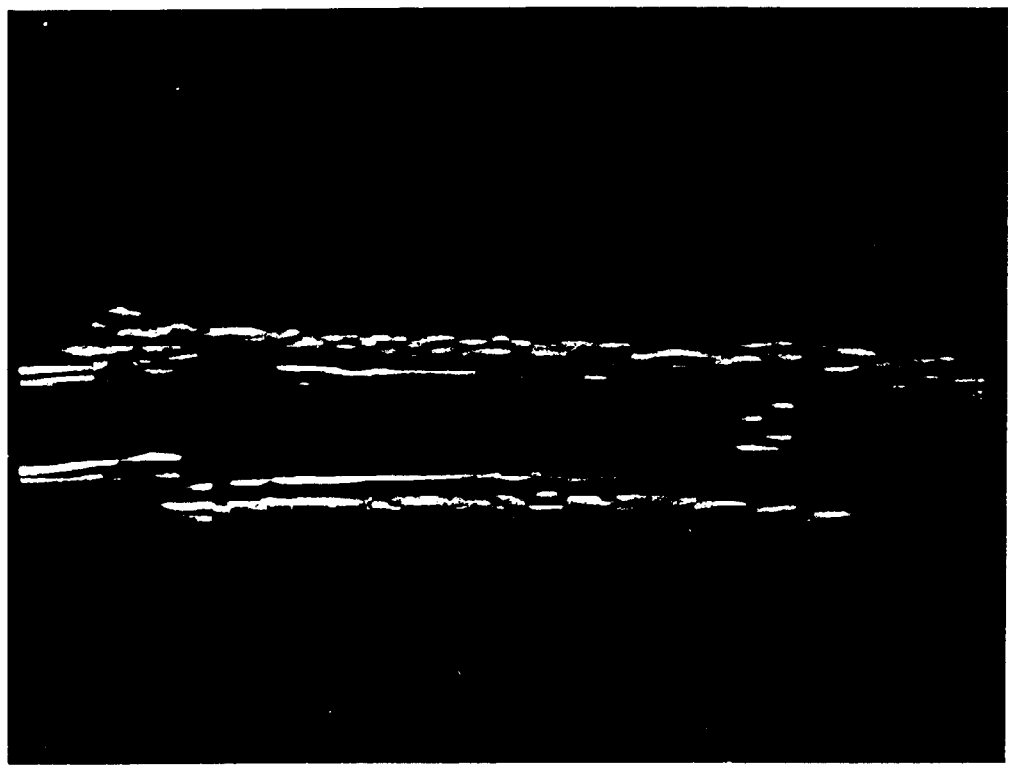

A successful non-invasive clot lysis procedure was conducted under the following conditions: driving frequency= 650 KHz, transducer excitation voltage=116 V, pulse repetition period, T=7 millisecond and pulse duration, τ=0.5 msec. Referring to FIG. 10A, an ultrasound image of a clot (right side) and buffer solution (dark left side) within a bovine vessel is shown. The focal point of the therapeutic transducer was advanced along the longitudinal axis of the artery segment from left to right. Ultrasound treatment was stopped at approximately the middle of the clot. Referring to FIG. 10B, it can be seen that the dark section indicative of liquid has grown from left to right in the vessel, and the clot has been reduced in size from the ultrasound treatment.

EXAMPLE 11

Measurements of acoustic emission (microphone output) in the audible range were conducted as a manifestation of the degree of cavitation activity by placing a microphone on a water filled tank. Referring to FIG. 11, microphone output was measured as a function of ultrasound peak intensity at T=7 ms, for both τ=0.070 ms and τ=0.100 ms. As shown in FIG. 11, a well defined threshold to the peak intensity was observed.

In addition, above the intensity threshold, the correlation between cavitation activity and intensity was linear. For data points corresponding to τ=70 μs, virtually no microphone output was observed until intensity exceeded approximately 1100 W/cm$^2$. For measurements made at τ=100 μs, virtually no microphone output (cavitation) was observed until ultrasound peak intensity exceeded about 600 W/cm$^2$.

As shown, cavitation activity increased with increased pulse duration. It was also observed that above the threshold, cavitation initiation was random, occurring in the range of I=600–2800 W/cm$^2$. However, if, for example, cavitation initiated at I=2,000 W/cm$^2$, microphone output would always be in the high range relative to if cavitation initiated at I=800 W/cm$^2$. It was also determined that after cavitation is initiated, the intensity can be decreased. Although cavitation activity will decrease, cavitation was maintained at the intensity shown in FIG. 11.

It was also determined that placing a microphone on the outside of the body of the subject receiving ultrasound treatments can provide an excellent method of obtaining feedback regarding whether cavitation is occurring. Thus, if an operator is applying ultrasound to a subject, he can watch or listen to a display from the microphone and determine whether cavitation is occurring under parameters where cavitation should be occurring. In addition, the microphone output can be fed to a data processor, which can display a warning signal or deactivate the ultrasound device if the device is fully powered, but cavitation is not being detected by the microphone. Also, the feedback can permit an operator to reduce power to the transducer to obtain the minimal amount of power needed to sustain cavitation.

EXAMPLE 12

Referring to FIG. 12, a comparison was conducted between cavitation activity produced in a buffer and in a clot for T=7 ms and τ=0.1 ms. Both the threshold and slope of the increase of cavitation activity with intensity were different for the buffer solution and the clot. The linear correlation (R) of the buffer and clot plots were R=0.94 and R=0.61, respectively.

After cavitation had been initiated the voltage could be decreased to decrease the ultrasound intensity, but maintain cavitation, i.e., it is an inertial phenomenon. Thus, in order to promote additional safety of operation, once cavitation of a clot has begun, the intensity can be decreased to maintain cavitation within the blood vessel but diminish a chance to injure the vessel itself.

Cavitation in blood and buffer solution was analyzed for degassed and non-degassed media. Operating conditions were T=7 msec and τ=0.1 msec. The cavitation threshold for a degassed medium is higher than in a non-degassed medium. Also, there was no difference in cavitation threshold between blood and the buffer solution for the parameters tested.

The cavitation threshold for non-degassed buffer and blood was in the range of 1000 to 1500 W/cm$^2$, closest to about 1200 W/cm$^2$. With respect to degassed buffer and blood, the cavitation threshold centered around 2000 W/cm$^2$.

The cavitation thresholds for non-degassed and degassed clots were also analyzed at T=7 msces and τ=0.1 msec. As with the above experiments, the cavitation threshold of a degassed sample was higher than the non-degassed sample.

EXAMPLE 13

Figure 13:
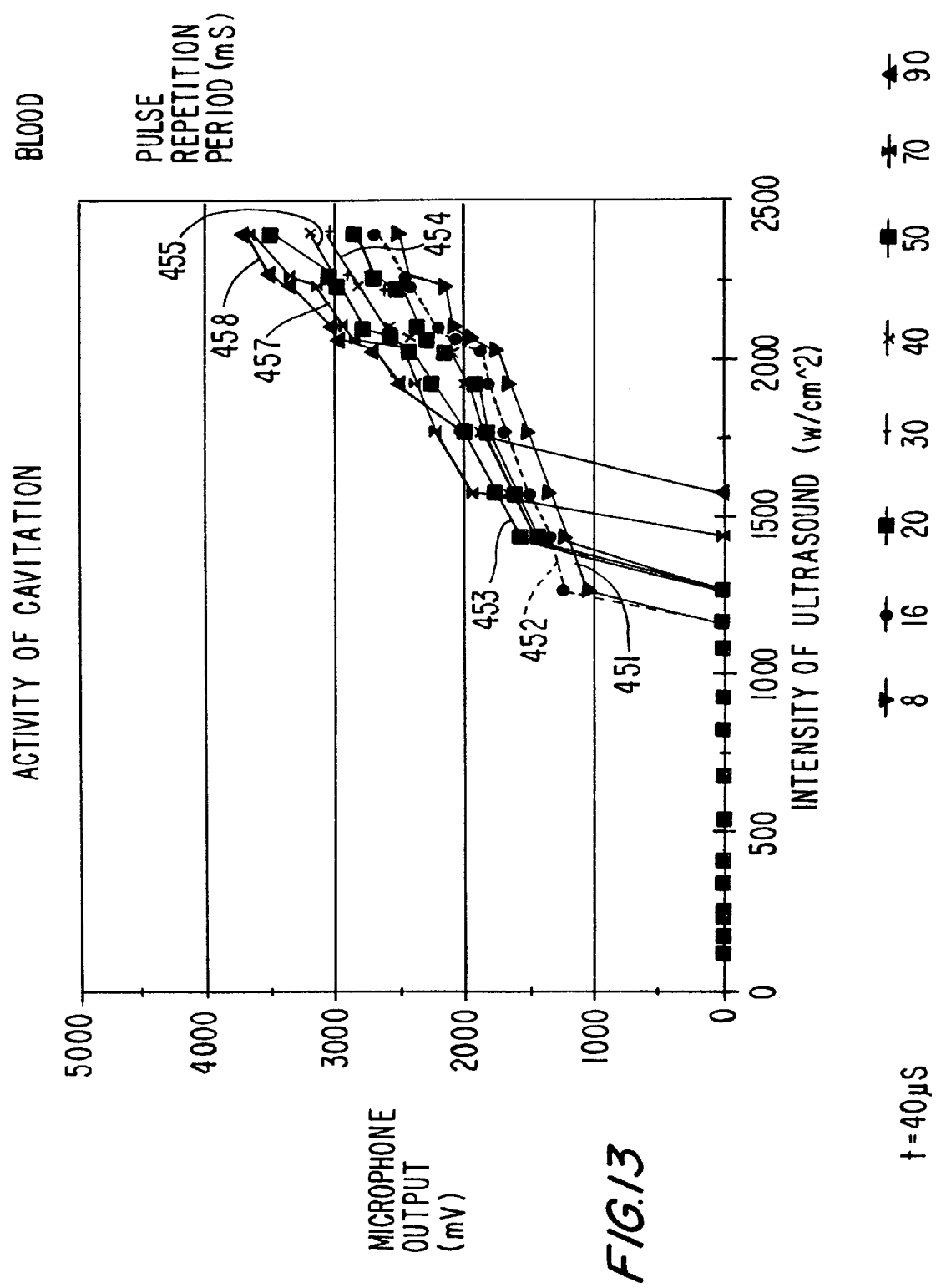
FIGS. 13 and 14 are graphs showing microphone output as a function of ultrasound intensity, when blood is acted upon by ultrasound of different pulse repetition periods (T), showing that shorter T's correlate to lower intensity thresholds and ultimately lower cavitation intensity.

Referring to FIG. 13, the activity of cavitation in blood, as a function of ultrasound intensity, was analyzed at τ=40

μs for pulse repetition periods of T=8 ms, 16 ms, 20 ms, 30 ms, 40 ms, 50 ms, 70 ms, and 90 ms as shown in curves 751–758, respectively. As shown in FIG. 13, there is an intensity threshold for inducing cavitation and the threshold was inversely proportional to pulse repetition period. For T=8 ms, cavitation occurred at an intensity of about I=1250 W/cm$^2$ and for T=90 ms, cavitation was first observed at I=1750 W/cm$^2$.

EXAMPLE 14

Figure 14:
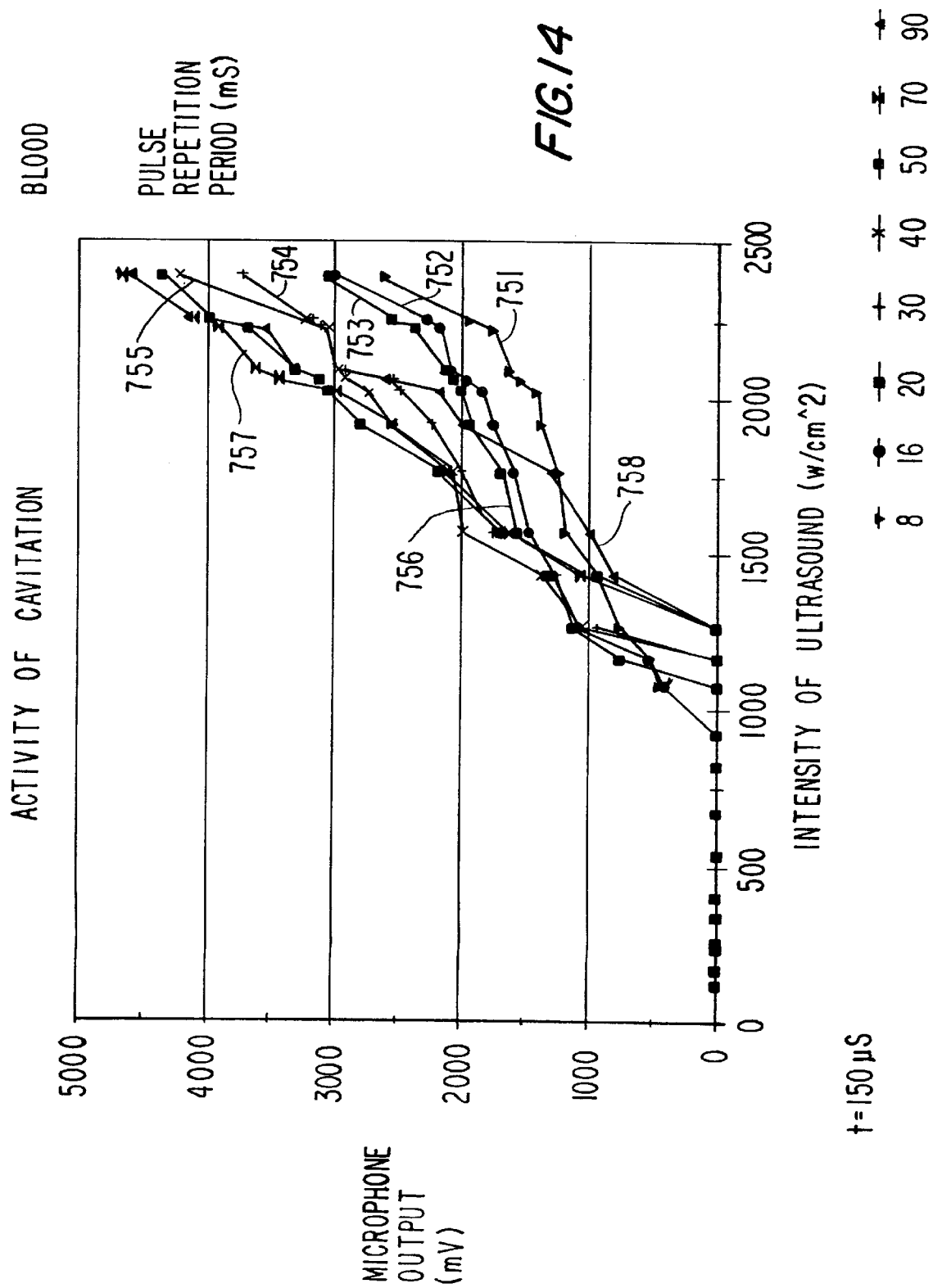

Referring to FIG. 14, an experiment similar to that discussed with reference to FIG. 13 was performed, in which blood was tested at τ=150 μs and pulse repetition periods of 8, 16, 20, 30, 40, 50, 70 and 90 ms, which are depicted by curves 451 through 458, respectively. Longer pulse repetition periods were associated with higher intensity requirements to initiate cavitation and higher cavitation activity.

EXAMPLE 15

Figure 15:
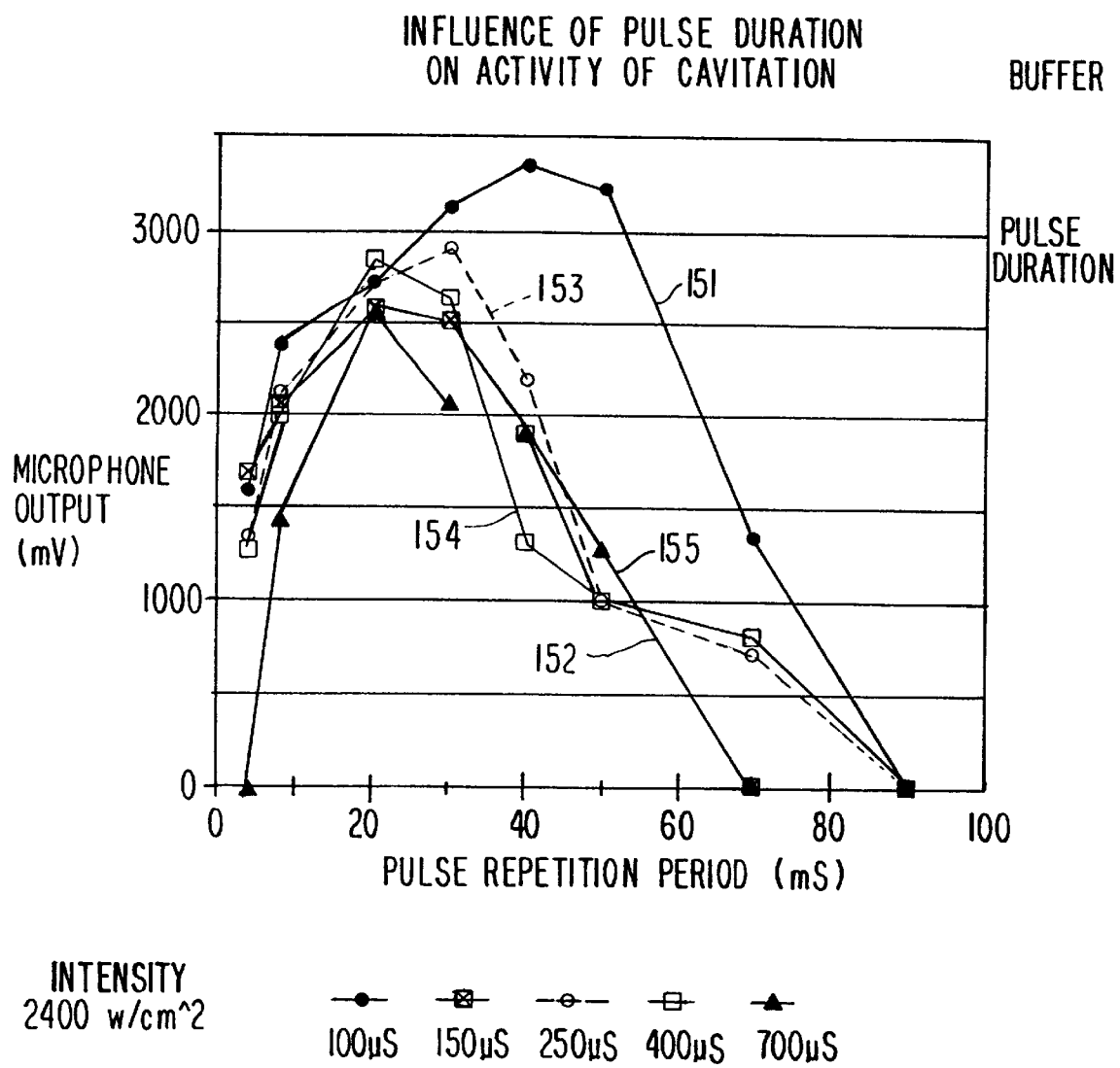
FIGS. 15 and 16 are graphs showing the influence of pulse duration on cavitation activity of a buffer solution and blood, respectively.

Referring to FIG. 15, the influence of pulse duration on cavitation activity was analyzed. Shorter pulse durations were associated with greater cavitation activity. Also, a pulse repetition period T=between about 10 and 50 ms created maximum cavitation activity for pulse durations from about 150 μs to about 700 μs, correlating to duty ratios ranging from about 15 to 500.

A buffer solution was subjected to ultrasound at an intensity of 2400 W/cm$^2$. The pulse repetition period was varied from about T=5 ms to about 90 ms for the following pulse durations: 0.100 ms (curve 151), 0.150 ms (curve 152), 0.250 ms (curve 153), 0.400 ms (curve 154), 0.700 ms (curve 155).

The experiment described above was repeated with pulse durations of 0.100 ms, 0.150 ms, 0.250 ms, 0.400 ms and 0.700 ms at an intensity I=2200 W/cm$^2$. The results are similar to those shown in FIG. 15, except that the cavitation activity decreased slightly with the decreased intensity. Maximum cavitation activity occurred in the range T<50 ms.

An experiment similar to that discussed above was performed at an intensity of I=2080 W/cm$^2$ at pulse durations of 0.100 ms, 0.150 ms, 0.250 ms, 0.400 ms. and 0.700 ms, respectively. Again, cavitation activity decreased with decreased ultrasound intensity and optimal pulse repetition periods were in the range T<40 ms. Shorter durations were associated with higher activity. As ultrasound intensity and hence cavitation activity decreased, the width of the range of optimal pulse repetition periods also decreased.

An experiment similar to that discussed with reference to FIG. 15 was performed, in which ultrasound intensity was set at I=1800 W/cm$^2$. Maximum cavitation occurred above T<30 for all but experiments run at a pulse duration of 0.700 μs, which exhibited cavitation to about T=50 ms.

EXAMPLE 16

Figure 16:
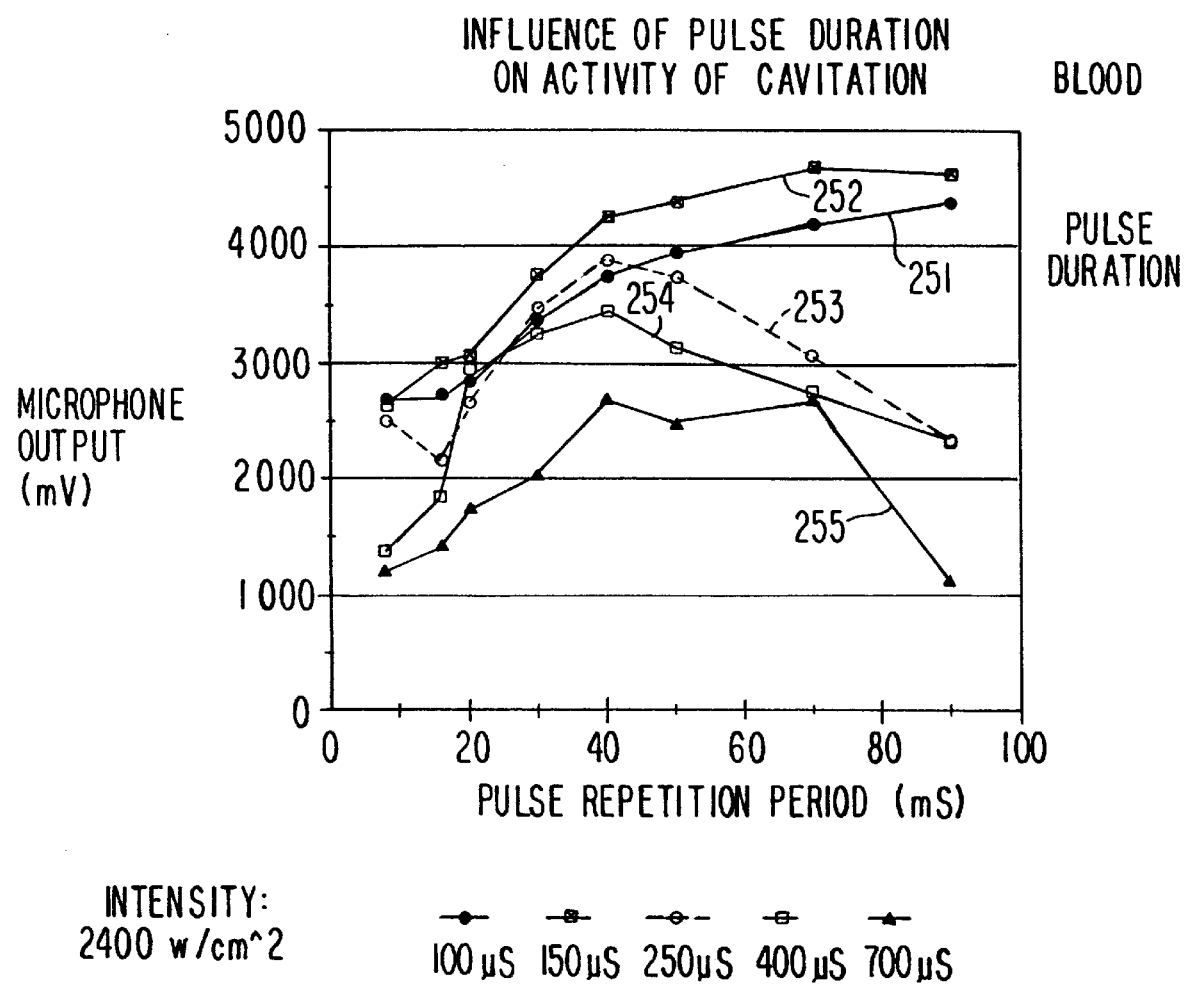

Another experiment similar to that discussed with reference to FIG. 15 was performed, except that the medium tested was blood, rather than a buffer solution. Referring to FIG. 16, the intensity was set at 2400 W/cm$^2$ and results are shown for pulse durations of 0.100 ms, 0.150 ms, 0.250 ms, 0.400 ms and 0.700 ms for curves 251, 252, 253, 254 and 255 respectively. The parameters for causing cavitation in blood were found to be different than those for causing cavitation in the buffer solution. For example, cavitation in blood was sustained over a much wider range of pulse repetition periods, to over T=100 ms. Again, however, the shorter pulse durations exhibited higher microphone output.

EXAMPLE 17

FIG. 17 shows cavitation as a function of pulse duration for a blood sample (curve 351) and a buffer sample (curve 352), at T=50 ms and intensity I=2400 W/cm$^2$. Optimal cavitation for the blood sample was in a pulse duration range of about τ=100 to 250 μs and a duty ratio of about 500 to about 200. It was evident that cavitation could still be achieved above τ=700 μs. For the buffer solution, the range of most effective pulse durations was narrower, and ranged from about 80 to about 150 μs. However, it was evident that cavitation would still occur above τ=700 μs.

The experiment discussed with reference to FIG. 17 was repeated at T=8 ms and the same intensity (2400 W/cm$^2$). The shorter pulse repetition periods slightly decreased the cavitation activity for the blood sample and increased the cavitation activity for the buffer sample, relative to the values shown in FIG. 17 and caused the cavitation activity for the buffer samples to be more similar. Cavitation was sustained from T=50 to 700 μs. Accordingly, different materials will exhibit different activity with respect to different pulse repetition periods. Thus, it can be advantageous to lyse a clot with parameters which cause high cavitation in blood, and will have a less pronounced effect on the blood vessel.

EXAMPLE 18

Referring to FIG. 18, the efficiency of clot lysis was analyzed by measuring percentage of clot weight loss as a function of ultrasound intensity for both a non-degassed (curve 551) and a degassed blood clot sample (curve 552). Lysis was performed with T=7 ms and τ=0.1 ms, at Vm=15 mm/min. Percentage of weight loss was determined by visual inspection and accordingly, the data are reasonable approximations. As shown in FIG. 18 the non-degassed clot was lysed at lower ultrasound intensities, with intensities above I=1600 W/cm$^2$ judged effective on the non-degassed sample and above I=2200 W/cm$^2$ on the degassed sample. Thus, the T and τ values and a duty cycle of 70 were deemed suitable.

EXAMPLE 19

Figure 19A:
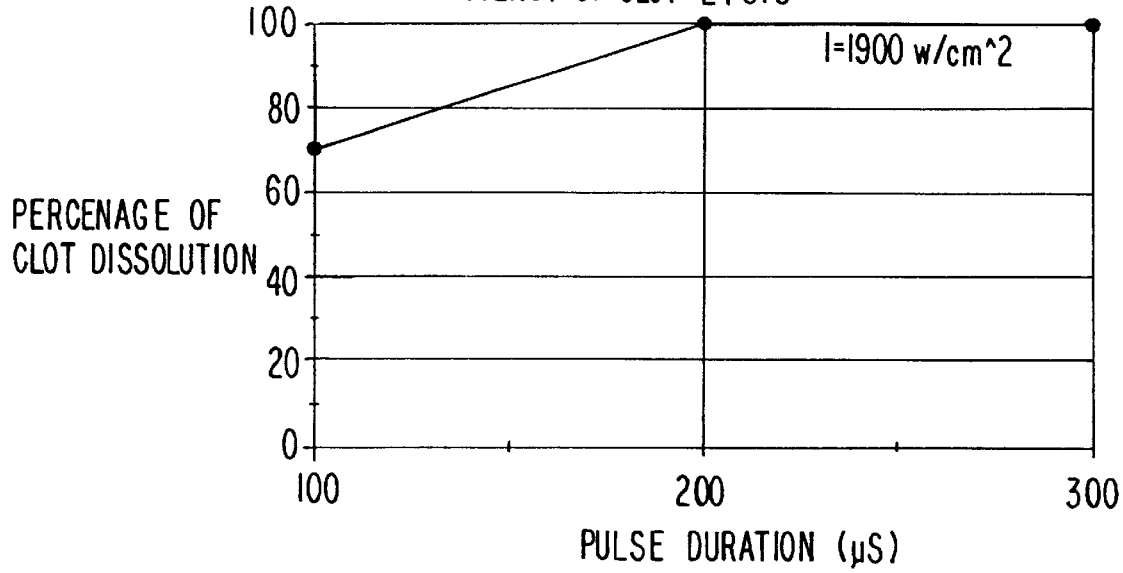
FIGS. 19A and 19B are two graphs showing percentage of clot dissolution as a function of pulse duration at two different power settings, at T=7 ms, showing increased clot dissolution with increased intensity and that optimal pulse durations exist for certain other parameters.
Figure 19B:
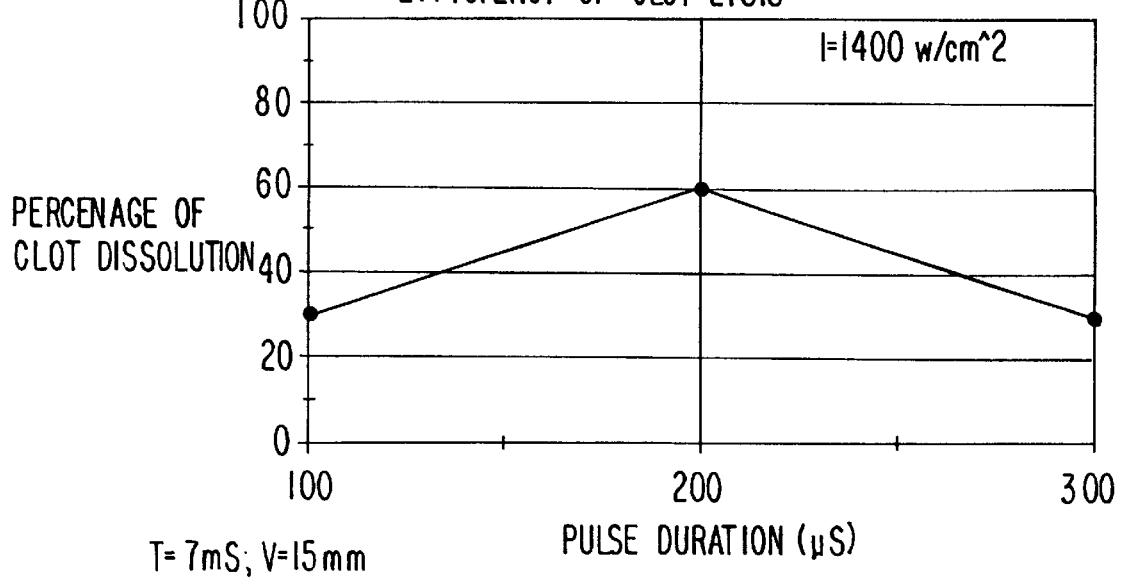

Referring to FIG. 19A, a clot was lysed at I=1900 W/cm$^2$ at pulse durations of 100, 200 and 300 μs. One hundred percent clot dissolution was achieved at 200 and 300 μs. Referring to FIG. 19B, under the same conditions, except for a reduction of intensity to I=1400 W/cm$^2$, optimum clot dissolution was achieved at τ=200 μs, with clot lysis at reduced efficiency at τ=100 and 300 μs. As shown, at lower intensities, high efficiency was achieved at T/τ=35, compared with T/τ=70 or 23.

Referring to FIG. 20A, at T=14 ms and V=15 mm/min and an intensity of I=1400 W/cm$^2$, the results of curve 571, were achieved. Referring to FIG. 20B, when τ was set at 200 μs, V was set at 10 mm/min and the pulse repetition period was varied from about 2.5 to 20, optimal clot dissolution was achieved at T=5 ms, or T/τ25, in a range of about 12 to 50, as shown by curve 572. Clot dissolution also be achieved above T=20 ms.

Referring to FIG. 20C, curve 581, T=5 ms, τ=0.2 ms and V=10 mm/min, pulse duration was varied from 100 μs to 300 μs at an ultrasound intensity of 1300 W/cm$^2$. Optimal efficiency was achieved at τ=200 μs, with the most efficient range from about 175 to 225 μs. Lysis was effective above τ=0.150 ms.

Referring to FIG. 21, curve 582, intensity of ultrasound was varied from about 900 W/cm$^2$ to about 1700 W/cm$^2$.

The cavitation threshold occurred at approximately 1250 W/cm² with maximum efficiency of intensities over 1300 W/cm² at T=5 ms and τ=0.2 ms. Increasing intensity maintained full clot dissolution.

EXAMPLE 20

Referring to FIG. 22, the efficiency of clot lysis was assessed by measuring the weight of unlysed clot after ultrasound application, as a function of ultrasound intensity. Parameters were T=5 ms, τ=0.2 ms, f=650 KHz, V=5 mm/min and intensity ranged up to 2500 W/cm². Unlysed clot material was separated with an 80 μm size filter. As shown in FIG. 22, above the threshold for clot lysis, only a small portion of the clot remained unlysed. At the parameters investigated, this intensity threshold was in the range 750 to 1250 W/cm².

The following examples present data illustrating from the application of ultrasound with a probe designed for the invasive application of ultrasound operated at about 44.4 KHz. Ultrasound was applied with a probe, similar to that depicted in U.S. Ser. No. 08/858,247, filed May 19, 1997 now U.S. Pat. No. 5,971,949 (the contents of which are incorporated herein by reference), having a proximal transducer coupled to an elongated transmission member with a distal tip constructed to cause cavitation within a blood vessel when activated by ultrasound transmitted from the transducer through the transmission member.

Figure 23:
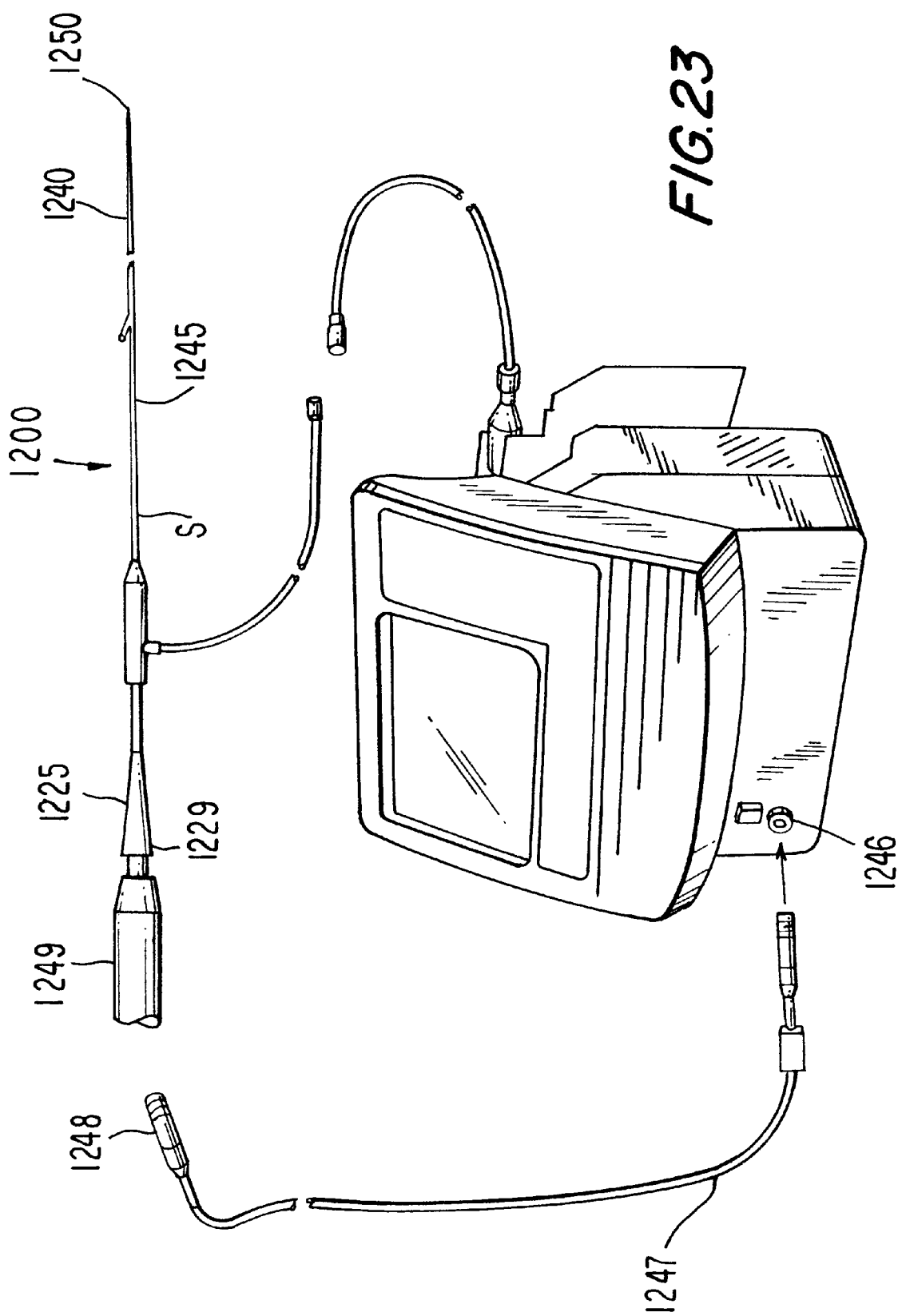
FIG. 23 is a perspective view of an invasive type ultrasound transmission system, constructed in accordance with an embodiment of the invention.

A non-limiting embodiment of an invasive-type ultrasound probe is illustrated generally as probe 1200 in FIG. 23, and in a copending application entitled COOLING SYSTEM FOR ULTRASOUND DEVICE under application Ser. No. 60/047,022, filed May 19, 1997, the contents of which are incorporated herein by reference.

Probe 1200 is formed with a tapered member 1225, formed with a proximal end 1229 of diameter $A_i$ constructed to be coupled to a source of ultrasound energy such as a transducer 1248. When coupled to a source of ultrasound energy, proximal end 1229 is preferably located at a displacement maximum relative to the standing ultrasound wave supported by the overall device. From proximal end 1229, tapered member 1225 tapers to a reduced diameter distal end of diameter $A_f$.

Proximal end 1229 must be large enough to receive sufficient energy to treat a thrombus, occlusions and the like. However, in order to provide optimal flexibility, it is desirable to reduce the diameter of distal portions of probe 1200 as much as possible, without significant loss of energy, strength or guidability. Furthermore, the reduction in diameter is preferably accomplished in such a manner as to amplify, or increase the amplitude of, the ultrasound vibrations.

Ultrasound device 1200 is understood to operate in the resonant frequency mode; i.e., it supports a standing wave when energized by ultrasonic stimulation at proximal end 1229. Consequently, it is preferred that a cavitation tip 1250 is located at a displacement maximum (anti-node).

To dissipate energy lost as heat, a probe in accordance with the invention can be bathed with a coolant. The coolant can be directed over and around the probe, for example, by incorporating a sheath 1245 around some or all sections of the probe. Sheathing 1245 may be affixed to the probe at one or more of the displacement nodes of the standing wave. Additional sheathing may be incorporated for providing a passageway for a guidewire or other auxiliary tool which may serve to steer or position the device to its intended location. Sheathing 1245 if formed of a high-strength, thin-walled, low-friction material, preferably polyimide.

Probe 1200 includes a horn 1225, having a tapered section T and a first constant diameter section S, is constructed to be coupled to an ultrasound energy source. Ultrasound energy is provided by the controller at a power source 1246 via a coaxial cable 1247 to a quick disconnect 1249, which connects coaxial cable 1247 to transducer 1248. Transducer 1248 is intimately connected to horn 1225. Probe 1200 also includes a transmission member 1240 coupled to horn 1225 and a tip 1250 coupled to the distal end of transmission member 1240. Ultrasound energy sources disclosed in U.S. Pat. No. 5,269,297, and in a copending application entitled FEEDBACK CONTROL SYSTEM FOR ULTRASOUND PROBE under application Ser. No. 60/046,938, filed May 19, 1997, the contents of which are incorporated herein by reference, are suitable.

Tip 1250 is coupled to three fine wires joining section 1240 and tip 1250 by means of three openings in tip 1250. In a preferred embodiment, the three openings in tip 1250 are spaced so as to form an equilateral triangle, concentric with the central axes of coupling tip 1250. Tip 1250 may also be provided with an opening for a guidewire, and a guidewire tube may be installed in the opening and extended proximally from the distal end. The fine wires may be separately sheathed, and any sheathing may extend between tip 1250 and a coupling joint. Wire 1240 may also be sheathed and the sheathing may be connected to the separate sheathing of the fine wires and may extend proximally to a coolant port through which coolant may be injected to bathe all or part of the transmission member.

The entire probe was placed in a straight configuration in a Plexiglas tube with an inner diameter of 3.5 mm and the tube was placed inside a water tank. A microphone was placed on the outside of the water tank and measured acoustic output which correlates to cavitation activity. The probe was operated in both continuous mode and pulse mode under various operating parameters and data was compiled.

EXAMPLE 21

Figure 24:
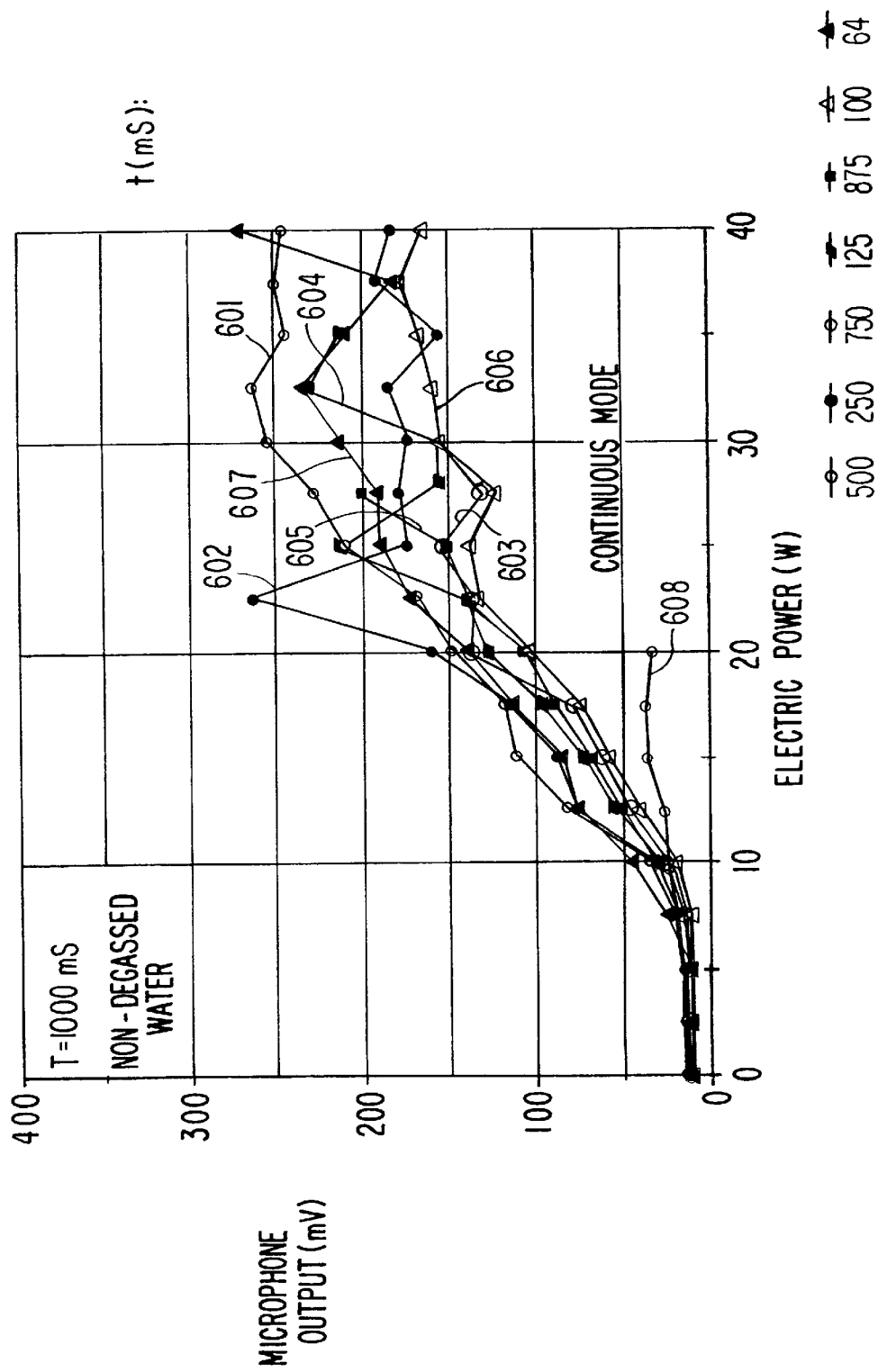
FIGS. 24–27 are graphs showing cavitation activity as a function of transducer power, showing the difference between continuous and pulsed activation.

Referring to FIG. 24, at T=1000 ms and τ=500, 250, 750, 125, 875, 164 ms, corresponding to curves 601–607 respectively and curve 608 corresponding to the probe activated in continuous mode, a cavitation threshold existed in the range 5 to 10 watts for pulsed mode of operation and non-degassed water.

EXAMPLE 22

An additional experiment was run in non-degassed water at T=500 ms and τ=250, 125, 64 and 32 ms. A control was also run in continuous mode. The results were similar to those shown in FIG. 24, with a threshold to cavitation in the range 10 to 20 watts and relatively no cavitation generated from operation in the continuous mode at up to 20 watts.

EXAMPLE 23

Figure 25:
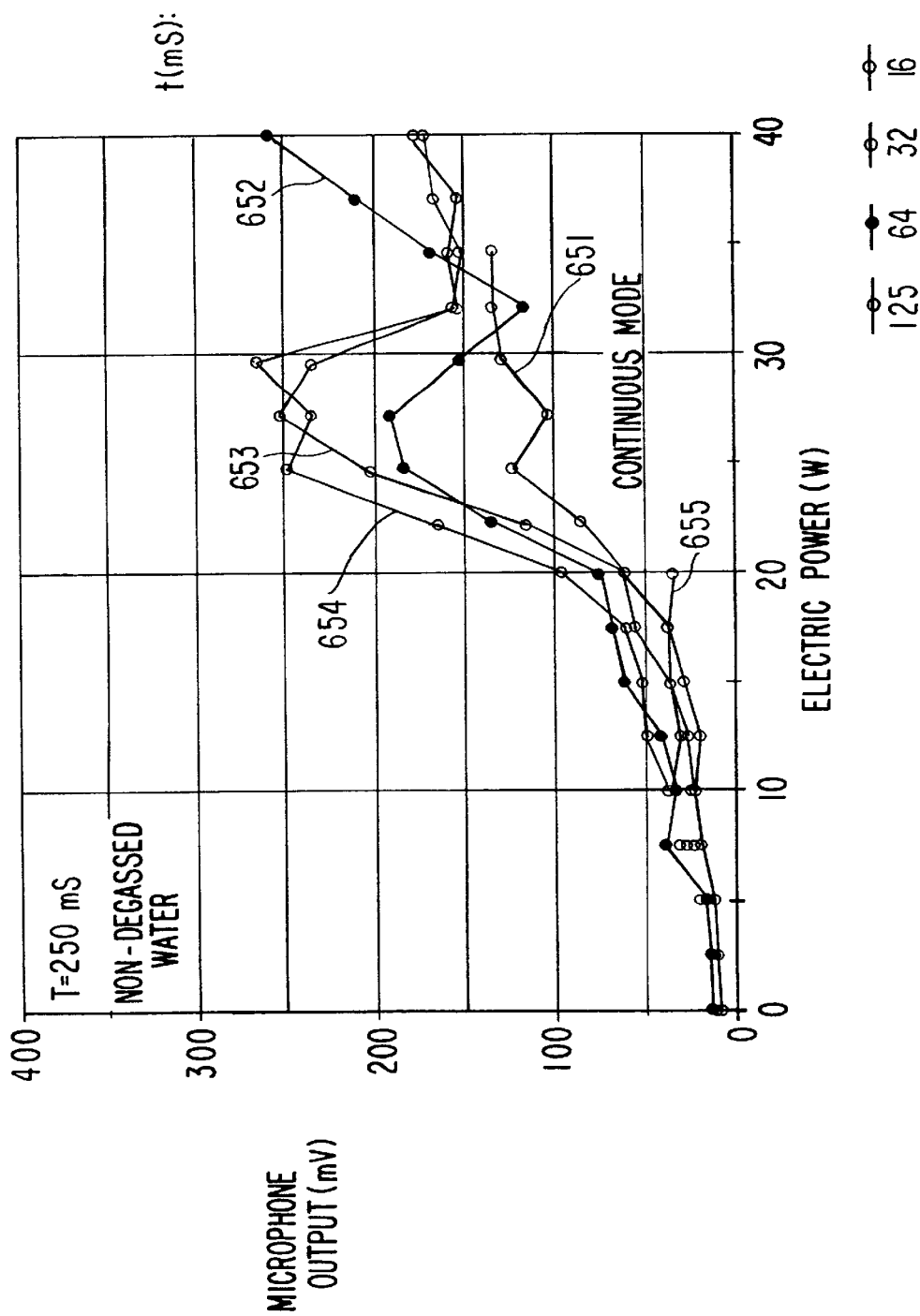

Referring to FIG. 25, an experiment similar to that discussed with reference to FIG. 24 was conducted, wherein non-degassed water received ultrasound from an invasive-type probe, but at T=250 ms. Electric power was increased over the range 0 to 40 watts at τ=125, 64, 32 and 16 ms, corresponding to curves 125, 64, 32 and 16 ms, corresponding to curves 651, 652, 653 and 654, respectively. Curve 655 shows operation in the continuous mode. As shown in FIG. 25, an ultrasound threshold occurred at about 20 watts and there was essentially no cavitation generated from the continuous mode operation at this power level.

EXAMPLE 24

Still another experiment was conducted, in which ultrasound was applied from an invasive-type transducer to non-degassed water at T=125 ms and τ=64, 32, 16 and 8 ms. Cavitation initiated in the range 15 to 20 watts for the pulse mode of operation, but not in the continuous mode operation, demonstrating advantages of pulsed operation in accordance with the invention.

EXAMPLE 25

Figure 26:
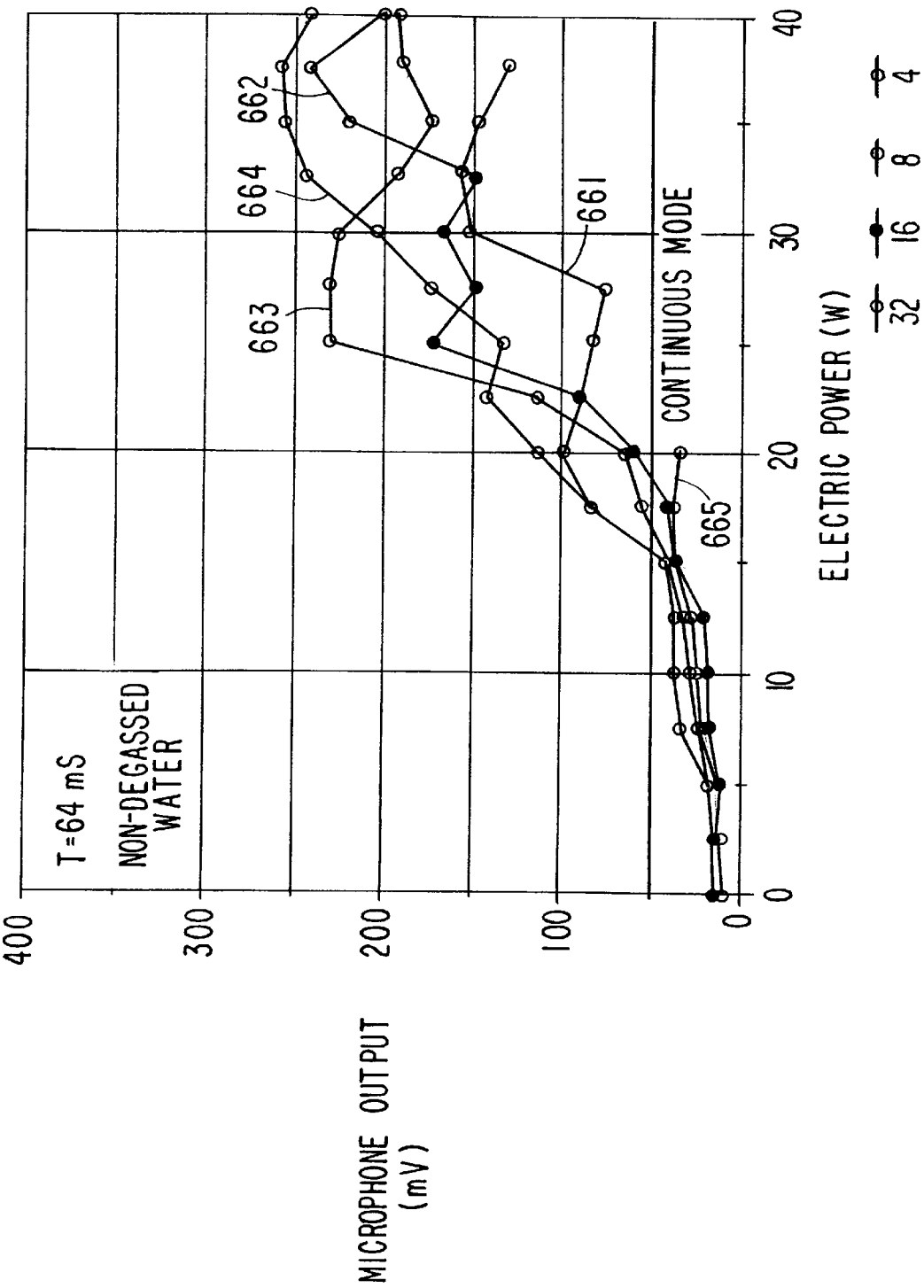

Referring to FIG. 26, the procedure discussed with reference to FIG. 24 was performed at T=64 ms. Pulse durations of τ=32, 16, 8, and 4 ms are shown in FIG. 25 as curves 661, 662, 663 and 664, respectively. Continuous mode operation is shown as curve 665. The cavitation threshold occurred in the range 15 to 20 watts for the pulsed mode of operation, but not the continuous mode of operation, demonstrating advantages of pulsed operation in accordance with the invention.

EXAMPLE 26

Figure 27:
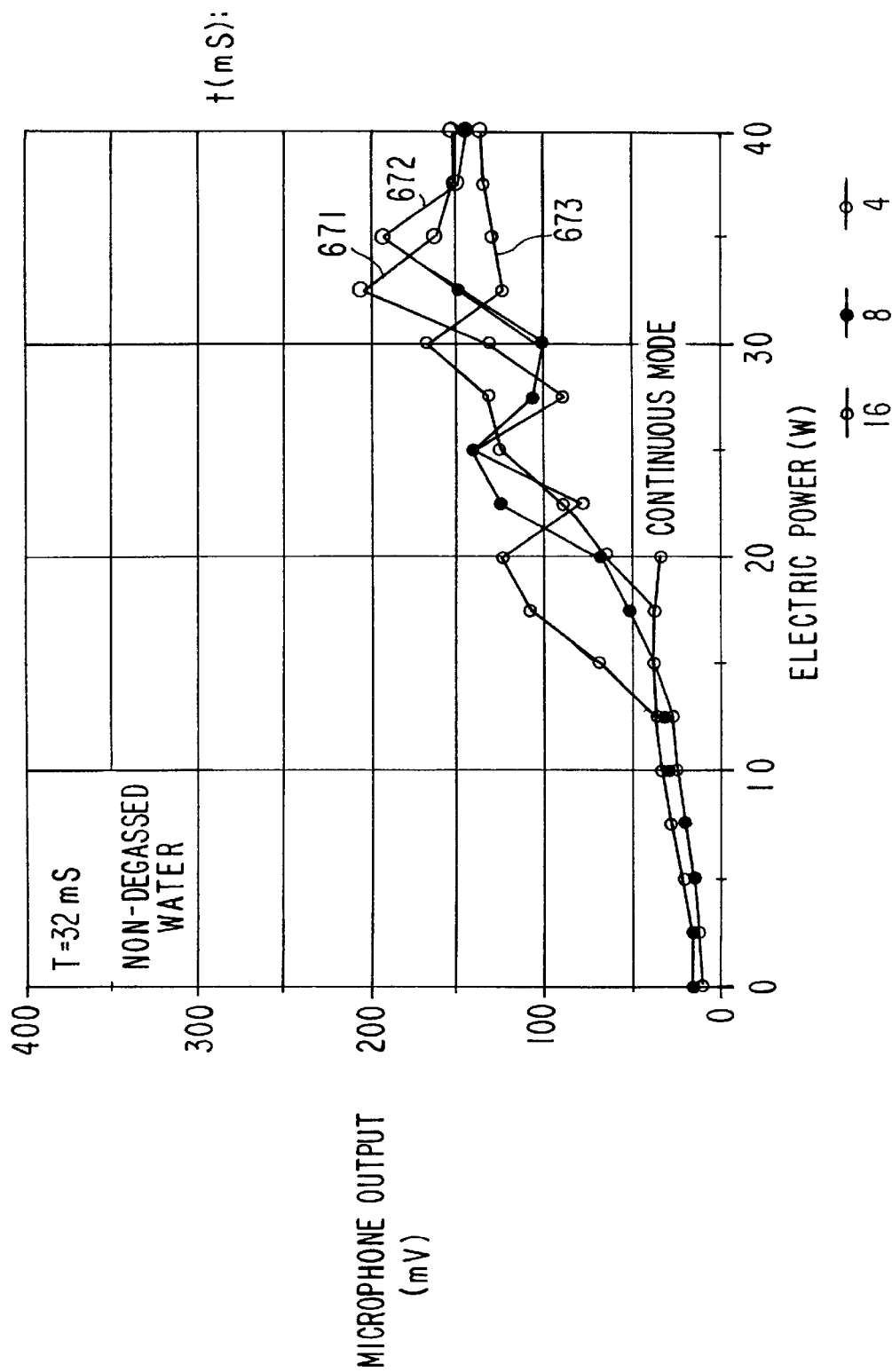

Referring to FIG. 27, the above procedure was repeated at T=32 ms and τ=16, 8 and 4 ms, corresponding to curves 671, 672 and 673, respectively. Continuous mode operation is shown by curve 674. A cavitation threshold occurred in the range of about 15 to 20 watts for pulsed operation, but with less overall cavitation activity than for some of the longer pulse durations. It is believed that the liquid medium requires a recovery period for optimum cavitation efficiency.

COMPARATIVE EXAMPLE 27

Figure 28:
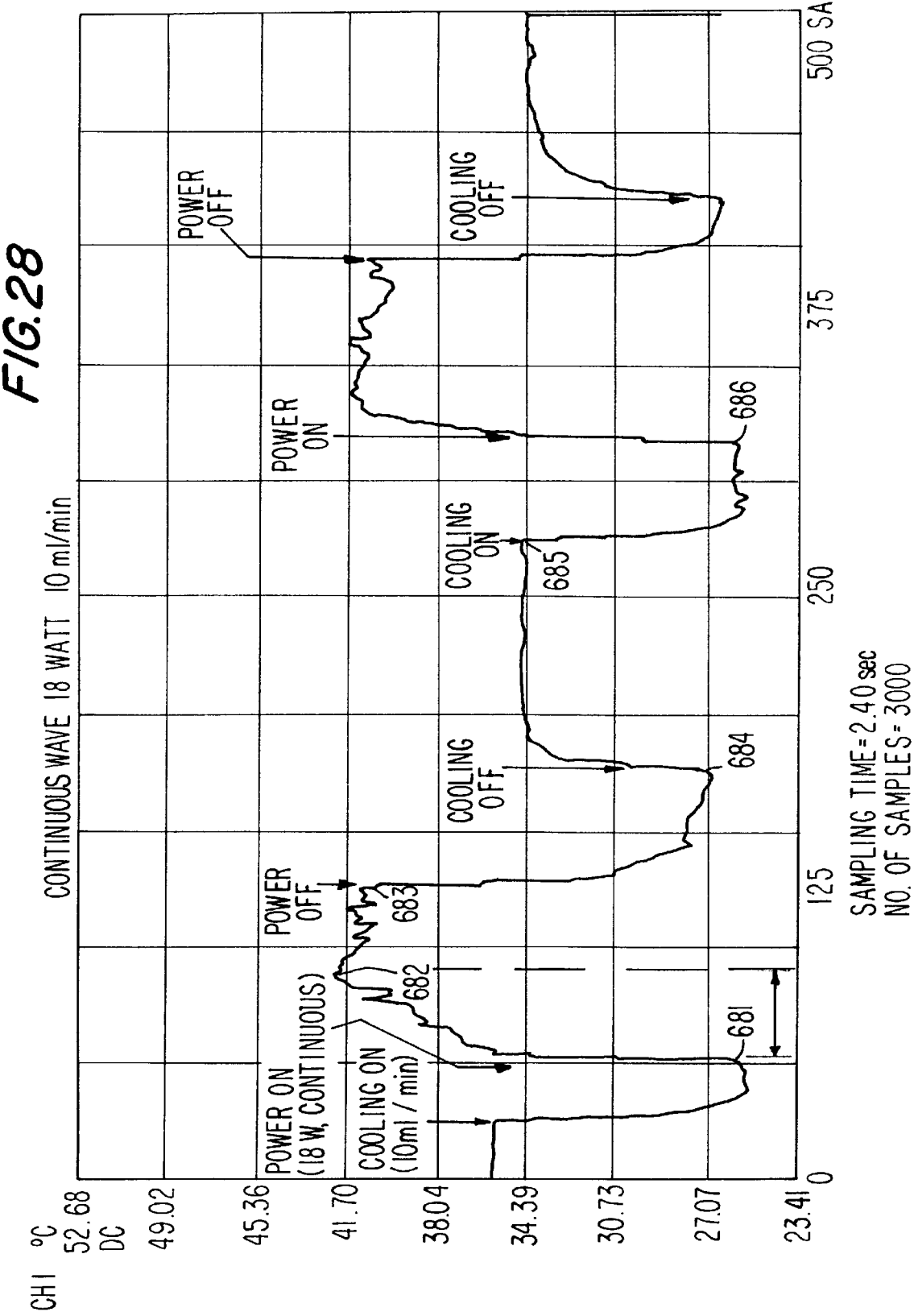

The invasive-type probe was operated under 18 watts of power. A thermocouple in contact with the tip inside the tube provided real time data with respect to temperature. Referring to FIG. 28, the system was initially at 37° C., 10 ml/min of 24° C. cooling water was pumped through the tube. As shown in FIG. 28, this reduced temperature at the probe tip to approximately 24° C. At point 681, the probe was turned on and activated with 18 watts of power. This quickly raised the temperature to over 41° C. (point 682).

At point 683, power was turned off and the temperature quickly returned to the cooling water temperature. At point 684, cooling water was turned off and the probe returned to approximately 34.4° C. At point 685, cooling water was turned on and the temperature of the probe quickly returned to approximately 27°.

At point 685, the probe was turned back on and the temperature quickly rose to above 41° C. After the power was turned off, the temperature of the probe returned to the temperature of the cooling water and then returned to the temperature of the tank after the cooling water was turned off.

EXAMPLE 28

Considerably different results were achieved when the probe was operated in pulse mode at a duty cycle of 8 (T=250 ms τ=32 ms) when 24° C. cooling water at 10 ml/min was turned on, the temperature of the probe quickly dropped to about 24° C. At point 691 power was turned on at a level of 20 watts. As shown in FIG. 29, the probe temperature increased to only slightly over 27° C., for a temperature increase of only about 3° C. At point 682, power to the probe was turned off and at point 683, the cooling water was turned off. At point 684, cooling water was turned back on and at point 685, power to the probe was turned back on. The probe was operated at 18 watts until it was turned off at point 686. As shown, probe temperature only increased about 2° C.

Similar results were achieved at a duty cycle of 16 (T=250, τ=16) (FIG. 30). At point 691, cooling water was turned on and at point 692, the probe was activated with 20 watts of power and turned off at point 693. As shown, probe temperature increased only 1 to 2° C. At point 694, cooling water was turned back on, the probe was turned on with 18 watts of power at point 696 and turned off at point 697. As shown, only a minimal increase in temperature occurred.

Tables 1 and 2 below provide evidence from additional experiments showing a minimal temperature rise when the probe is operated in a pulsed mode, particularly at a duty cycle ratio of 8 or more. In view of their minimal temperature increase using the described pulsing parameters in conjunction with the lower cavitation threshold and high cavitation activity, it is believed that invasive-type probes can be operated without cooling fluid and also, without a covering sheath. This will permit the use of substantially smaller guide catheters in view of an overall reduction in the outer dimensions of the probe. Another advantage is a considerable reduction in metal fatigue.

TABLE 1

Study on the temperature rise at different flow rates of the cooling buffer and at different excitation modes.

| # | Flow Rate | Duty Cycle | Power | Temp Rise | Max Temp |
|---|---|---|---|---|---|
| 1 | 10 | Continuous | 18 | 16.8 | 41.7 |
| 2 | 10 | Continuous | 18 | 15.4 | 41 |
| 3 | 10 | 8 | 20 | 2.4 | 28.1 |
| 4 | 10 | 8 | 18 | 1.7 | 27.6 |
| 5 | 10 | 16 | 20 | 1.2 | 27.1 |
| 6 | 10 | 16 | 18 | 0.7 | 26.6 |
| 7 | 10 | 8 | 30 | 4.6 | 31.8 |
| 8 | 10 | 8 | 30 | 4.1 | 31.6 |
| 9 | 10 | 8 | 40 | 5.3 | 33.3 |
| 10 | 10 | 8 | 40 | 5.3 | 33.3 |
| 11 | 10 | 16 | 30 | 3.8 | 29.7 |
| 12 | 10 | 16 | 30 | 4.1 | 29.2 |
| 13 | 10 | 16 | 40 | 4.8 | 30.8 |
| 14 | 10 | 16 | 40 | 4.6 | 30.7 |
| 15 | 5 | 8 | 30 | 8.2 | 35 |
| 16 | 5 | 8 | 30 | 8.4 | 35 |
| 17 | 5 | 8 | 30 | 7.2 | 36.2 |
| 18 | 5 | 8 | 30 | 7.2 | 36.1 |
| 19 | 5 | 16 | 30 | 4.6 | 33.5 |
| 20 | 5 | 16 | 30 | 4.3 | 33.5 |
| 21 | 5 | 16 | 40 | 8.2 | 37.5 |
| 22 | 5 | 16 | 40 | 6.2 | 34.1 |
| 23 | 2.5 | 16 | 30 | 3.7 | 35.7 |
| 24 | 2.5 | 16 | 30 | 4.1 | 35.7 |
| 25 | 0 | 16 | 20 | 3.1 | 39.8 |
| 26 | 0 | 16 | 20 | 3.1 | 39.8 |
| 27 | 0 | 16 | 30 | 4.6 | 41.1 |
| 28 | 0 | 16 | 30 | 4.1 | 40.9 |
| 29 | 0 | 16 | 40 | Destruction | — |
| 30 | 10 | Continuous | 18 | 16.1 | 45.8 |
| 31 | 10 | Continuous | 18 | 16.8 | 44.3 |
| 32 | 10 | Continuous | 18 | 17.8 | 45.3 |
| 33 | 10 | 16 | 18 | 2.2 | 30 |
| 34 | 10 | 16 | 18 | 1.7 | 30.5 |
| 35 | 10 | 16 | 18 | 2.6 | 29.8 |
| 36 | 10 | 8 | 18 | 1.2 | 29.9 |
| 37 | 10 | 8 | 18 | 1.2 | 29.9 |
| 38 | 10 | 8 | 18 | 1.2 | 29.9 |
| 39 | 5 | 16 | 18 | 1.5 | 31.8 |
| 40 | 5 | 16 | 18 | 1.7 | 32.1 |
| 41 | 5 | 16 | 18 | 1.5 | 31.9 |
| 42 | 0 | 16 | 18 | 2.4 | 39.6 |
| 43 | 0 | 16 | 18 | 2.4 | 39.6 |

TABLE 1-continued

Study on the temperature rise at different flow rates of the cooling buffer and at different excitation modes.

| # | Flow Rate | Duty Cycle | Power | Temp Rise | Max Temp |
|---|---|---|---|---|---|
| 44 | 0 | 16 | 18 | 2.6 | 39.8 |
| 45 | 0 | 16 | 18 | 2.6 | 39.8 |
| 46 | 0 | 16 | 18 | 2.6 | 39.8 |
| 47 | 0 | 16 | 18 | 2.6 | 39.8 |
| 48 | 10 | 16 | 18 | 1 | 28.8 |
| 49 | 10 | 16 | 18 | 1.2 | 29.1 |
| 50 | 10 | 16 | 18 | 1.2 | 29.1 |
| 51 | 5 | 16 | 18 | 1.5 | 31.4 |
| 52 | 5 | 16 | 18 | 1.7 | 31.4 |
| 53 | 5 | 16 | 18 | 1.7 | 31.4 |
| 54 | 10 | 8 | 18 | 1.2 | 28.9 |
| 55 | 10 | 8 | 18 | 1 | 29.1 |
| 56 | 10 | 8 | 18 | 1.2 | 29.4 |
| 57 | 10 | Continuous | 18 | 16.6 | 43.9 |
| 58 | 10 | Continuous | 18 | 16.1 | 43.6 |
| 59 | 10 | Continuous | 18 | 16.6 | 43.6 |

Clot lysis — Cell function manipulation (eg. migration, adhesion, etc.)
Plaque ablation — Drug delivery manipulation
Coagulation — Drug activity enhancement
Cancer treatment — Biological product manipulation (eg. genes, anti-sense DNA)
Phonopheresis
Induction of Apoptosis — Molecule manipulation
Induction of Necrosis — Cavitation initiation manipulation
Liposuction — Cavitation sustaining manipulation
Heat generation manipulation It will thus be seen that the objects set forth above, among those made apparent from the preceding description, are efficiently attained and, since certain changes may be made in the above composition of matter without departing from the spirit and scope of the invention, it is intended that all matter contained in the above description shall be interpreted as illustrative and not in a limiting sense.

It is also to be understood that the following claims are intended to cover all of the generic and specific features of

TABLE 2

Study on the temperature rise at different flow rates of the cooling buffer and at different excitation modes.

| # | Flow Rate ml/min | Duty Cycle | Pulse Rep. Period (mS) | Pulse Length (mS) | Power (watt) | Frequency (KHz) | Temperature Rise (grad) | Max Temp (grad) |
|---|---|---|---|---|---|---|---|---|
| 1 | 10 | Continuous | — | — | 18 | 44.6 | 16.1 | 41.3 |
| 2 | 10 | 8 | 256 | 32 | 20/18 | 44.6 | 2.4/1.7 | 27.9 |
| 3 | 10 | 16 | 256 | 16 | 20/18 | 44.6 | 1.2/1.0 | 26.9 |
| 4 | 10 | 8 | 256 | 32 | 30 | 44.4 | 4.6 | 31.7 |
| 5 | 10 | 8 | 256 | 32 | 40 | 44.4 | 4.8 | 33.3 |
| 6 | 10 | #6 | 256 | 16 | 30 | 44.4 | 2.9 | 29.5 |
| 7 | 10 | 16 | 256 | 16 | 40 | 44.4 | 4.3 | 38 |
| 8 | 5 | 8 | 256 | 32 | 30 | 44.4 | 7.9 | 35 |
| 9 | 5 | 8 | 256 | 32 | 30 | 44.3 | 7.2 | 36.2 |
| 10 | 5 | 16 | 256 | 16 | 30 | 44.3 | 3.8 | 33.5 |
| 11 | 5 | 16 | 256 | 16 | 40 | 44.3 | 7 | 36 |
| 12 | 2.5 | 16 | 256 | 16 | 30 | 44.3 | 3.8 | 35.7 |
| 13 | 0 | 16 | 256 | 16 | 20 | 44.3 | 3.1 | 39.8 |
| 14 | 0 | 16 | 256 | 16 | 30 | 44.3 | 4.3 | 41 |
| 15 | 0 | 16 | 256 | 16 | 40 | 44.3 | Destruction | — |
| 16 | 10 | Continuous | — | — | 18 | 44.5 | 16.9 | 45 |
| 17 | 10 | 16 | 256 | 16 | 18 | 44.5 | 2.2 | 30 |
| 18 | 10 | 8 | 256 | 32 | 18 | 44.5 | 1.2 | 29.9 |
| 19 | 5 | 16 | 256 | 16 | 18 | 44.5 | 1.6 | 31.9 |
| 20 | 0 | 16 | 256 | 16 | 18 | 44.5 | 2.5 | 39.7 |
| 21 | 10 | 16 | 256 | 16 | 18 | 44.5 | 1.1 | 29 |
| 22 | 5 | 16 | 256 | 16 | 18 | 44.5 | 1.6 | 31.4 |
| 23 | 10 | 8 | 256 | 32 | 18 | 44.5 | 1.1 | 29.1 |
| 24 | 10 | Continuous | — | — | 18 | 44.5 | 16.4 | 43.8 |

It is understood that the techniques described for the invasive and non-invasive application of ultrasound are also applicable to systems that promote or focus ultrasound energy to enhance the absorption of drugs, induce apoptosis in cells, and/or treat tissue, tumors, obstructions, and the like, within and without the body, systems to be utilized in or for laproscopic surgery, for ultrasonic scalpels, and to induce tissue hyperthermia such as for cancer radiation therapy, for example. Furthermore, drugs, such as streptokinase, urokinase, whose function or efficacy would be enhanced by ultrasound or that would enhance the application of ultrasound at the treatment site, may be infused within the coolant fluid for cooling the ultrasound probe or delivered through a separate passageway within or without the ultrasound probe to the treatment site.

The following is a partial list of applications for pulsed ultrasound:

the invention herein described and all statements of the invention which, as a matter of language, might be said to fall therebetween.

What is claimed is:

1. A method of applying therapeutic ultrasound to a location within a body, comprising: activating a transducer to produce ultrasound at a pulse repetition period of $T \leq 1000$ milliseconds and directing this ultrasound to a location within a body and at appropriate power, frequency and pulse duration, to generate cavitation at the location.

2. The method of claim 1, wherein the ultrasound is directed to a location within the body in an invasive manner, with an ultrasound device which is inserted into the body.

3. The method of claim 2, wherein T=about 1 millisecond to 1000 milliseconds.

4. The method of claim 1, including the steps of initiating cavitation within the body by applying a first amount of power to the transducer, initiating cavitation at the location within the body, then reducing the power supplied, while maintaining cavitation.

5. A method of applying therapeutic ultrasound to a location within a body, comprising: producing ultrasound with a pulse duration of $\tau \leq 100$ milliseconds and transmitting the ultrasound to a location within a body via a transmission member which is at least partially inserted into the body and applying said ultrasound under conditions of appropriate power, frequency pulse duration $\tau$ and pulse repetition period T, so as to generate cavitation at the location.

6. The method of claim 5, wherein the frequency of the ultrasound produced in about 20 to 100 KHz.

7. The method of claim 6, wherein $\tau$ is about 10–100 milliseconds.

8. The method of claim 5, wherein the pulse repetition period $T \leq$ about 1000 milliseconds.

9. The method of claim 8, wherein T is about 100 to 500 milliseconds.

10. The method of claim 9, wherein $\tau$ is about 10–100 milliseconds.

11. The method of claim 10, wherein the frequency of the ultrasound produced is about 20–100 KHz.

12. The method of claim 10, wherein the ultrasound is produced with a transducer operated at a peak power output of 10 to 40 watts.

13. The method of claim 9, wherein the ultrasound is produced with a transducer operated at a peak power output of 10 to 40 watts.

14. The method of claim 5, wherein $\tau$ is about 20–60 milliseconds.

15. The method of claim 14, wherein the ultrasound is produced with a transducer operated at a peak power output of about 15 to 30 watts.

16. The method of claim 14, wherein substantially no cooling fluid is pumped around the transmission member.

17. The method of claim 5, wherein the ultrasound is produced with a transducer operated at a peak power output of 10 to 40 watts.

18. The method of claim 17, wherein the peak power output is about 15 to 30 watts.

19. The method of claim 5, wherein the device is operated at a pulse repetition period $T \leq$ about 1000 milliseconds and at a duty ratio $T/\tau$ about $\geq 5$.

20. The method of claim 5, wherein the device is operated at a pulse repetition period $T \leq$ about 1000 milliseconds and at a duty ratio $T/\tau$ about $\geq 8$.

21. The method of claim 5, including the steps of inserting a guide catheter within the body and positioning the transmission member within the guide catheter, wherein the transmission member is substantially unsheathed within the guide catheter and transmitting the ultrasound to the location within the body via the unsheathed transmission member.

22. A method of applying therapeutic ultrasound to a location within a body, comprising: activating a transducer to produce ultrasound at a pulse repetition period of $T \leq 1000$ milliseconds and directing this ultrasound to a location within a body; initiating cavitation at the location within the body by applying a first amount of power to the transducer, then reducing the power supplied, while maintaining cavitation.

23. The method of claim 22, wherein the ultrasound is directed to a location within the body in an invasive manner, with an ultrasound device which is inserted into the body.

24. The method of claim 23, wherein T=about 1 millisecond to 1000 milliseconds.

25. The method of claim 22, wherein the frequency of the ultrasound produced in about 20 to 100 KHz.

26. The method of claim 22, including the step of producing ultrasound with a pulse duration of $\tau \leq 100$ milliseconds and transmitting the ultrasound to a location within a body via a transmission member which is at least partially inserted into the body.

27. The method of claim 26, wherein T is about 100 to 500 milliseconds.

28. The method of claim 26, wherein $\tau$ is about 20–60 milliseconds.

29. The method of claim 26, wherein $\tau$ is about 10–100 milliseconds.

30. The method of claim 27, wherein $\tau$ is about 10–100 milliseconds.

31. The method of claim 30, wherein the frequency of the ultrasound produced is about 20–100 KHz.

32. The method of claim 31, wherein the ultrasound is produced with a transducer operated at a peak power output of 10 to 40 watts.

* * * * *

(12) EX PARTE REEXAMINATION CERTIFICATE (6177th)
United States Patent
Rosenschein et al.

(10) Number: US 6,113,558 C1
(45) Certificate Issued: Apr. 8, 2008

(54) PULSED MODE LYSIS METHOD

(75) Inventors: Uri Rosenschein, Kefar Daniel (IL); Yoram Eshel, Tel Aviv (IL); Vladimir Furman, Ashelon (IL); Efim Kerner, Rehovot (IL)

(73) Assignee: Tulchinsky Stern Trust Co. Ltd., Jerusalem (IL)

Reexamination Request:
No. 90/006,339, Jul. 29, 2002

Reexamination Certificate for:
Patent No.: 6,113,558
Issued: Sep. 5, 2000
Appl. No.: 08/939,289
Filed: Sep. 29, 1997

(51) Int. Cl.
*A61B 17/22* (2006.01)
*A61B 17/00* (2006.01)
*A61B 18/00* (2006.01)

(52) U.S. Cl. .................................. 601/2; 606/128
(58) Field of Classification Search ............... 601/2–4; 606/1, 128, 169; 604/22; 600/439
See application file for complete search history.

(56) References Cited

U.S. PATENT DOCUMENTS 5,209,221 A * 5/1993 Riedlinger .................. 601/2

OTHER PUBLICATIONS

Vykhodtseva et al. "Histologic Effects of High Intensity Pulsed Ultrasound Exposure with Subharmonic Emission in Rabbit Brain In Vivo," (1995), Ultrasound in Med. & Biol. vol. 21, No. 7, pp. 969–979.*

Ter Harr et al. "Evidence for Acoustic Cavitation in Vivo: Thresholds for Bubble Formation with 0.75 MHz Continuous Wave and Pulsed Beams," (1986) IEEE Transaction on Ultrasonics, Ferroelectrics, and Frequency Control, vol. UFFC–33 No. 2 pp. 162–164.*

* cited by examiner

*Primary Examiner*—Eleni Mantis Mercader

(57) ABSTRACT

An apparatus and method for the application of ultrasound to a location within the body is provided. The apparatus can advantageously operate at a pulse duration below about 100 milliseconds and in the range 0.1 milliseconds to 100 milliseconds and a pulse repetition period below about 1 second and in the range of 1 millisecond to 1 second. Duty ratios over 5 and preferably over 8 are also advantageous. Therapeutic applications of ultrasound such as for assisting in the treatment of medical conditions such as cancer and/or other ailments are also provided.

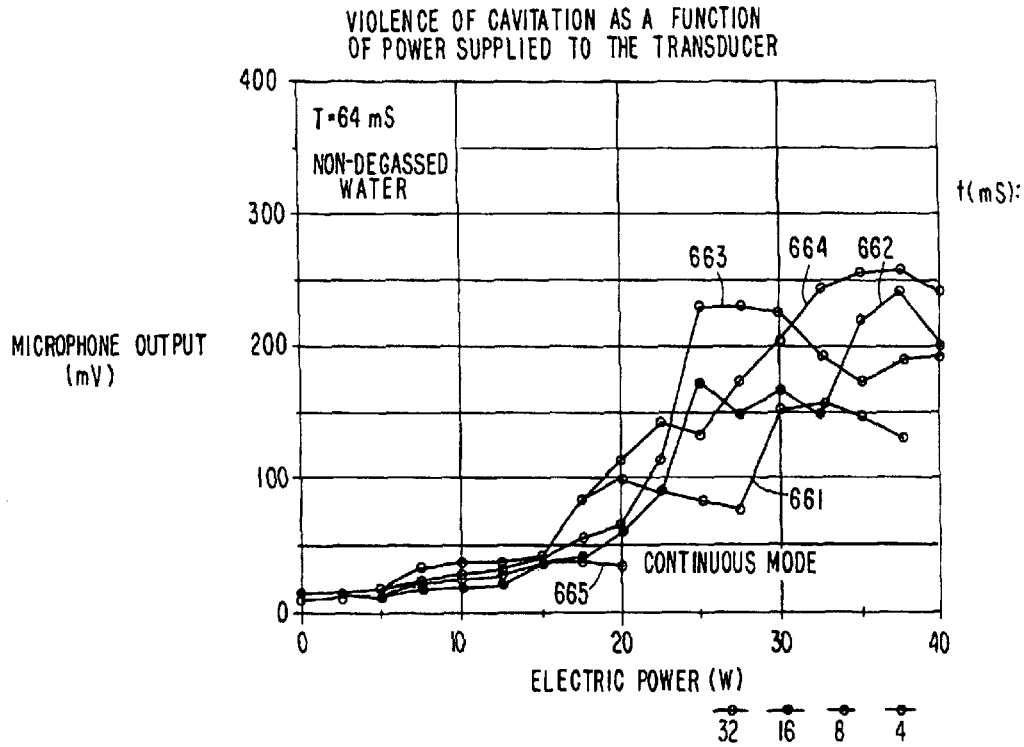

EX PARTE
REEXAMINATION CERTIFICATE
ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 5–18, 20 and 21 is confirmed.

Claims 3 and 19 are cancelled.

Claims 1, 22 and 26 are determined to be patentable as amended.

Claims 2, 4, 23–25 and 27–32, dependent on an amended claim, are determined to be patentable.

New claims 33–47 are added and determined to be patentable.

1. A method of applying therapeutic ultrasound to a location within a *human* body, comprising: activating a transducer to produce ultrasound at a pulse repetition period of T≦1000 milliseconds, *a pulse duration τ, where 100 microseconds ≦τ≦1.1 millisecond and at a duty ratio T/τ about ≧5* and directing this ultrasound to a location within a body and at appropriate power, frequency, and pulse duration to generate cavitation at the location.

22. A method of applying therapeutic ultrasound to a location within a *human* body, comprising: activating a transducer to produce ultrasound at a pulse repetition period of T≦1000 milliseconds, *a pulse duration τ, where 100 microseconds ≦τ≦1.1 millisecond and at a duty ratio T/τ about ≧5* and directing this ultrasound to a location within a body; initiating cavitation at the location within the body by applying a first amount of power to the transducer, *and* then reducing the power supplied, while maintaining cavitation.

26. [The] *A* method of [claim 22] *applying therapeutic ultrasound to a location within a body comprising: activating a transducer to produce ultrasound at a pulse repetition rate period of T≦1000 milliseconds and directing this ultrasound to a location within a body; initiating cavitation, at the location within the body by applying a first amount of power to the transducer, and then reducing the power supplied while maintaining cavitation,* including the step of producing ultrasound with a pulse duration of τ≦100 milliseconds and transmitting the ultrasound to a location within a body via a transmission member which is at least partially inserted into the body.

33. The method of claim 1 wherein τ is ≦700 microseconds.

34. The method of claim 33 wherein τ≧150 microseconds.

35. The method of claim 1 wherein τ is ≦250 microseconds.

36. The method of claim 1 wherein τ is ≦1 millisecond.

37. The method of claim 22 wherein τ is ≦700 microseconds.

38. The method of claim 37 wherein τ≧150 microseconds.

39. The method of claim 22 wherein τ is ≦250 microseconds.

40. The method of claim 22 wherein τ is ≦1 millisecond.

41. A method of applying therapeutic ultrasound to a location within a body, comprising: activating a transducer to produce ultrasound at a pulse repetition period of T≦1000 milliseconds and directing this ultrasound to a location within the body and at appropriate power, frequency and pulse duration, to generate cavitation at the location, wherein the ultrasound is directed to a location within the body in an invasive manner, with an ultrasound device which is inserted into the body.

42. The method of claim 33, wherein T=about 1 millisecond to 1000 milliseconds.

43. The method of claim 33, including the steps of initiating cavitation within the body by applying a first amount of power to the transducer, initiating cavitation at the location within the body, and then reducing the power supplied, while maintaining cavitation.

44. A method of applying therapeutic ultrasound to a location within a body, comprising: activating a transducer to produce ultrasound at a pulse repetition period of T≦1000 milliseconds, directing this ultrasound to a location within the body, initiating cavitation at the location within the body by applying a first amount of power to the transducer, and then reducing the power supplied, while maintaining cavitation wherein the ultrasound is directed to a location within the body in an invasive manner, with an ultrasound device which is inserted into the body.

45. The method of claim 36, wherein T=about 1 millisecond to 1000 milliseconds.

46. The method of claim 36, wherein the frequency of the ultrasound produced in about 20 to 100 KHz.

47. A method of applying therapeutic ultrasound to a location within a body, which method comprises the steps of:
   activating a transducer to produce ultrasound at a pulse repetition period of T≦1000 milliseconds.
   directing the ultrasound to a location within a body,
   initiating cavitation at the location by applying a first amount of power to the transducer, and
   reducing the power supplied to the transducer for pulses applied after cavitation is initiated while maintaining cavitation.

* * * * *